US009063159B2

(12) United States Patent
Herman et al.

(10) Patent No.: US 9,063,159 B2
(45) Date of Patent: Jun. 23, 2015

(54) LC-MS SEPARATION AND DETECTION OF VITAMIN D METABOLITES

(75) Inventors: Joseph L. Herman, West Chester, PA (US); Dayana Argoti, Charlestown, MA (US)

(73) Assignee: Cohesive Technologies Inc., Franklin, MA (US)

(*) Notice: Subject to any disclaimer, the term of this patent is extended or adjusted under 35 U.S.C. 154(b) by 0 days.

(21) Appl. No.: 13/881,843

(22) PCT Filed: Oct. 28, 2011

(86) PCT No.: PCT/US2011/058423
§ 371 (c)(1),
(2), (4) Date: Nov. 5, 2013

(87) PCT Pub. No.: WO2012/058614
PCT Pub. Date: May 3, 2012

(65) Prior Publication Data
US 2014/0147878 A1      May 29, 2014

Related U.S. Application Data

(60) Provisional application No. 61/408,385, filed on Oct. 29, 2010.

(51) Int. Cl.
*G01N 33/00*    (2006.01)
*G01N 33/82*    (2006.01)

(52) U.S. Cl.
CPC ............ *G01N 33/82* (2013.01); *G01N 2560/00* (2013.01); *Y10T 436/203332* (2015.01)

(58) Field of Classification Search
USPC ............................ 436/131; 250/282; 552/653
See application file for complete search history.

(56) References Cited

U.S. PATENT DOCUMENTS

| | | | |
|---|---|---|---|
| 4,292,250 A * | 9/1981 | DeLuca et al. ............... | 536/18.1 |
| 5,772,874 A | 6/1998 | Quinn et al. | |
| 5,795,469 A | 8/1998 | Quinn et al. | |
| 5,919,368 A | 7/1999 | Quinn et al. | |
| 5,968,367 A | 10/1999 | Quinn et al. | |
| 7,700,365 B2 | 4/2010 | Singh et al. | |
| 7,745,226 B2 | 6/2010 | Clarke et al. | |
| 7,888,000 B2 * | 2/2011 | Thierry-Palmer et al. ........ | 435/4 |
| 2011/0195513 A1 | 8/2011 | Calton et al. | |
| 2013/0143329 A1 * | 6/2013 | Holmquist et al. ........... | 436/131 |

FOREIGN PATENT DOCUMENTS

WO          2012058614           5/2012

OTHER PUBLICATIONS

Higashi T. et al. Liquid Chromatography—Tandem Mass Spectrometric Method for the Determination of Salivary 25-Hydroxyvitamin D3. Anal Bioanal Chem 391:229-238, 2008.*

Saenger A. et al. Quantification of Serum 25-Hydroxyvitamin D2 and D3 Using HPLC-Tandem MS and Examination of Reference Intervals for Diagnosis of Vitamin D Deficiency. Am J Clinical Path 125:914-920, 2006.*

Trenerry V C et al, "The determination of vitamin D3 in bovine milk by liquid chromatography mass spectrometry", Food Chemistry, Elsevier Ltd, NL., Oct. 10, 2010, pp. 1314-1319, XP027504503, vol. 125, No. 4.

Maunsell Z et al, "Routine isotope-dilution liquid chromatography-tandem mass spectrometry assay for simultaneous measurement of the 25 hydroxy metabolites of vitamins D2 and D3", Clinical Chemistry, American Association for Clinical Chemistry, Washington DC, Sep. 1, 2005, pp. 1683-1690, XP003005459, vol. 51, No. 9.

Vogeser M et al., "Candidate reference method for the quantification of circulating 25-hydroxyviatamin D3 by liquid chromatography-tandem mass spectrometry", Clinical Chemistry, American Association for Clinical Chemistry, Washington DC, Aug. 1, 2004, pp. 1415-1417, XP003005458, vol. 50, No. 8.

Ying Yu et al., "Identification and Structural Elucidation of Vitamin D3 Metabolites in Human Urine Using LC-MS-MS", Chromatographia; An International Journal for Rapid Communication in Chromatography, Electrophoresis and Associated Techniques, Vieweg Verlag, WI., Nov. 26, 2008, pp. 103-109, XP019666676, vol. 69, No. 1-2.

Herman J L., "Generic approach to high throughput ADME screening for lead candidate optimization", International Journal of Mass Spectrometry, Elsevier Science Publishers, Amsterdam, NL, Nov. 1, 2004, pp. 107-117, XP004639193, vol. 238, No. 2.

Gracia-Lor E et al., "Simultaneous determination of acidic, neutral and basic pharmaceuticals for urban wastewater by ultra high-pressure liquid chromatography-tandem mass spectrometry", Journal of Chromatography, Elsevier Science Publishers B.V., NL, Jan. 29, 2010, pp. 622-632, XP026827421, vol. 1217, No. 5.

Lan Gao et al., "A generic fast solid-phase extraction high-performance liquid chromatography/mass spectrometry method for high-throughput drug discovery", Rapid Communications in Mass Spectrometry, Nov. 15, 2007, pp. 3497-3504, XP55018911, vol. 21, No. 21.

Gros M et al., "Development of a multi-residue analytical methodology based on liquid chromatrography-tandem mass spectrometry (LC-MS/MS) for screening and pharmaceuticals in surface and wastewaters", Talanta, Elxevier, Amersterdam, NL, Nov. 15, 2006, pp. 678-690, XP025000808, vol. 70, No. 4.

(Continued)

*Primary Examiner* — Ralph Gitomer
(74) *Attorney, Agent, or Firm* — Workman Nydegger

(57)  ABSTRACT

Systems, kits, and methods for quantitation of metabolites of vitamin D by liquid chromatography-mass spectrometry (LC-MS). The systems, kits, and methods described herein stabilize and/or promote the formation of the protonated molecular ion ([M+H]+) for the vitamin D metabolites in the ionization source (e.g., electrospray ionization ("ESI")). Formation of the molecular ion does not involve loss of a water molecule from the parent molecule. Subsequent fragmentation of the [M+H]+ ion yields product ions that are specific to each molecular ion. The systems, kits, and methods described herein provide for no compromise in specificity and provide for a significant increase in sensitivity relative to previously described methods.

5 Claims, 12 Drawing Sheets

(56) References Cited

OTHER PUBLICATIONS

Maurer H H., "Multi-analyte procedures for screening for and quantification of drugs in blood, plasma, or serum by liquid chromatography-single stage or tandem mass spectrometry (LC-MS or LC-MS/MS) relevant to clinical and forensic toxicology", Clinical Biochestry, Elsevier Inc., US, CA, Apr. 1, 2005, pp. 310-318, XP004781808, vol. 38, No. 4.

Zimmer et al., "Comparison of Turbulent-Flow Chromatography with Automated Solid-Phase Extraction in 96-Well Plates and Liquid-Liquid Extraction Used as Plasma Sample Preparation Techniques for Liquid Chromatography-Tandem Mass Spectrometry," Journal of Chromatography 854:23-35, 1999.

Capote et al. "Identification and Determination of Fat-Soluble Vitamins and Metabolites in Human Serum by Liquid Chromatography/Triple Quadrupole Mass Spectrometry with Multiple Reaction Monitoring," Rapid Communications in Mass Spectrometry, 2007, 21: 1745-1754.

Taylor et al. "Simultaneous Quantification of Tacrolimus and Sirolimus in Human Blood, by High-Performance Liquid Chromatography-Tandem Mass Spectrometry," Therapeutic Drug Monitoring, 2000, 22:608-612.

Salm et al. "The Quantification of Sirolimus by High-Performance Liquid Chromatography-Tandem Mass Spectrometry and Microparticle Enzyme Immunoassay in Renal Transplant Recipients," Clinical Therapeutics, vol. 22, Suppl. B 2000 pp. B71-B85.

\* cited by examiner

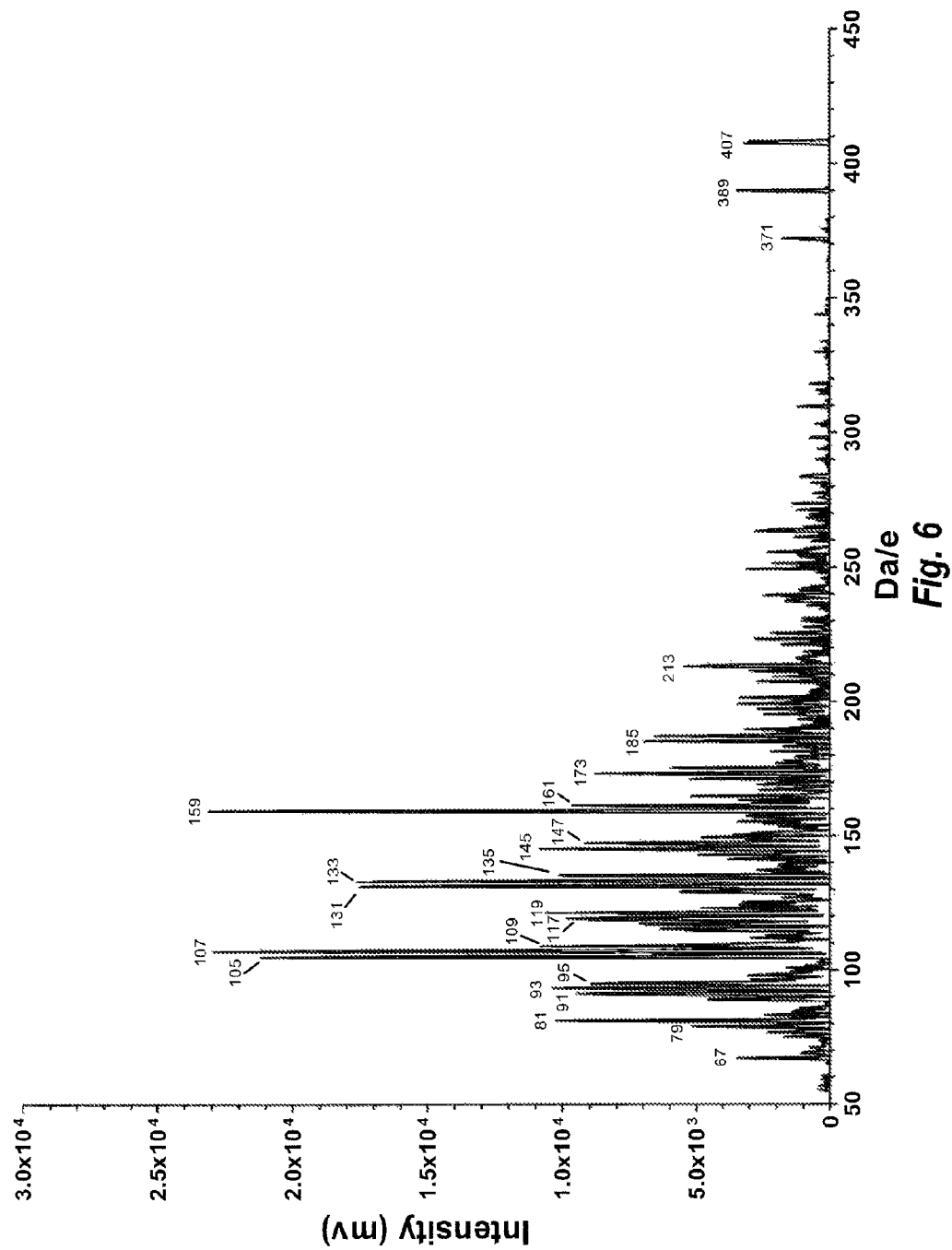

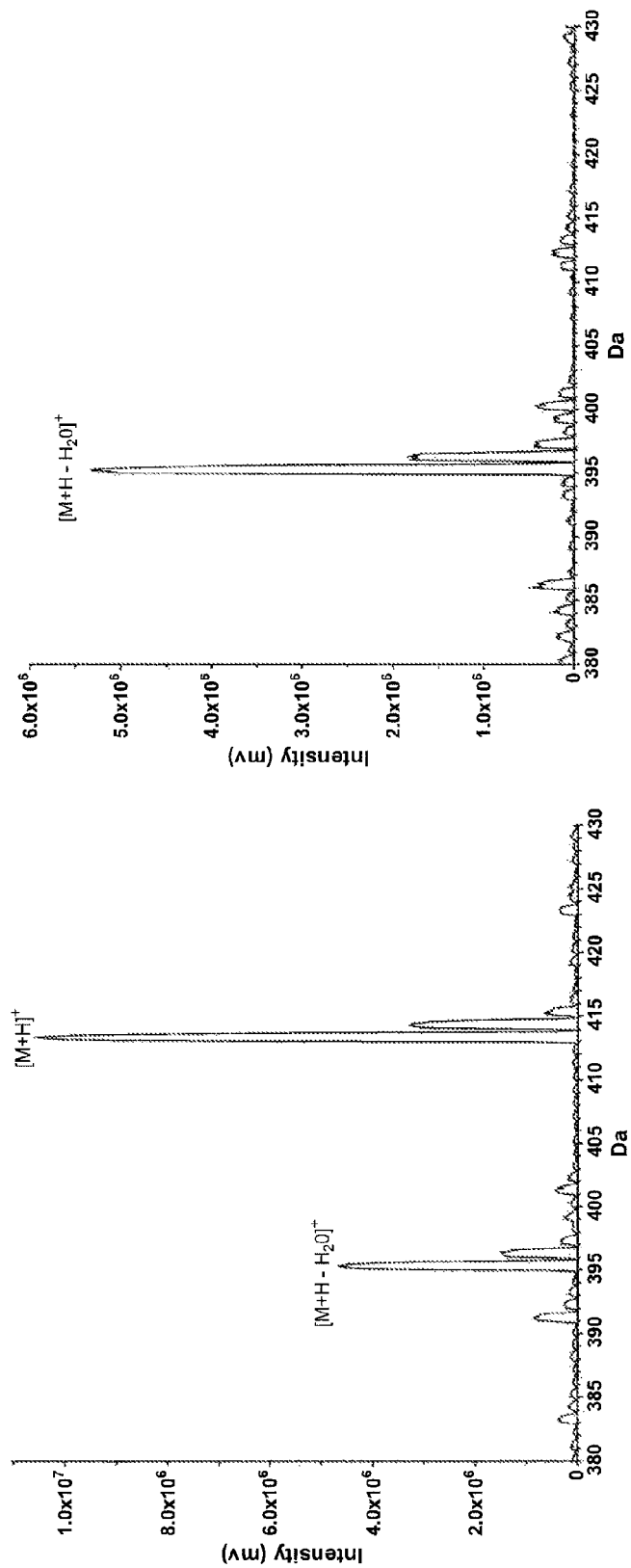

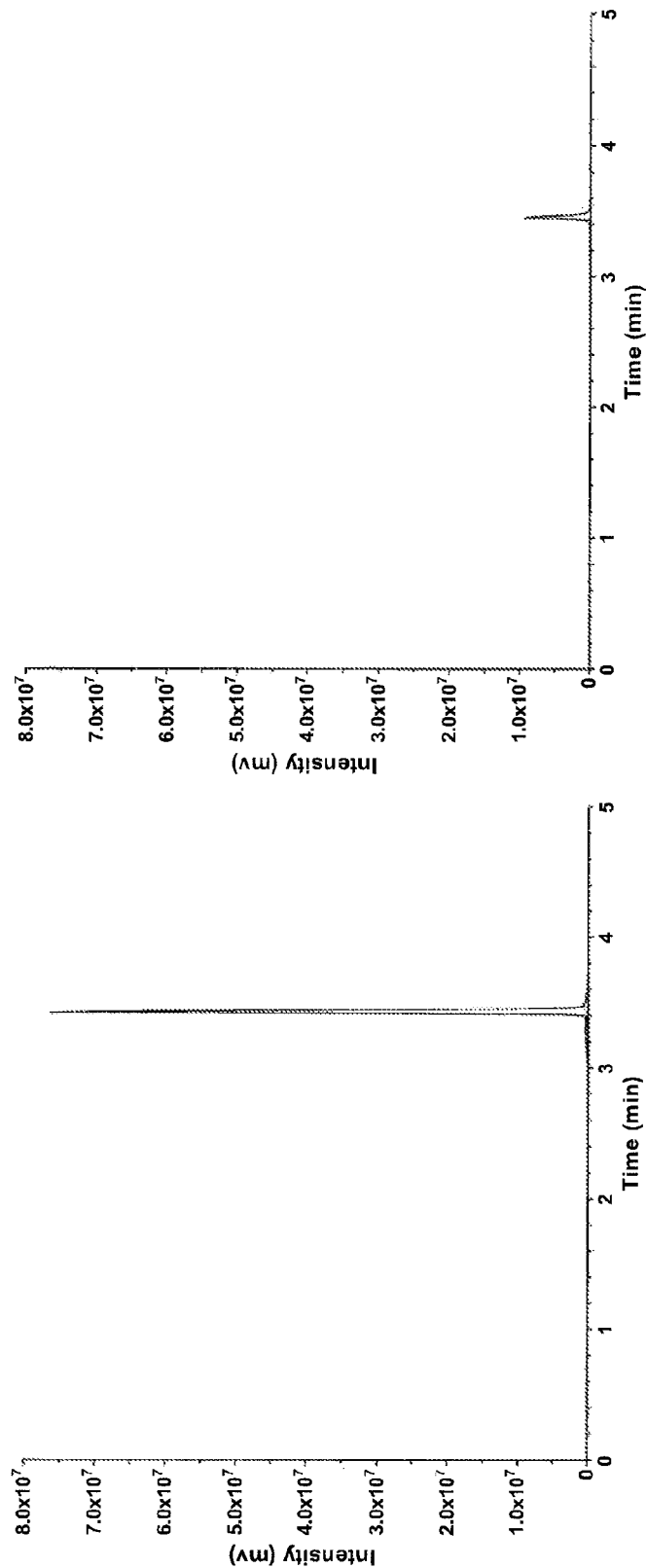

LC-MS SEPARATION AND DETECTION OF VITAMIN D METABOLITES

CROSS-REFERENCE TO RELATED APPLICATIONS

This application claims the benefit of and priority to PCT Application Serial No. PCT/US2011/058423, filed 28 Oct. 2011, entitled "LC-MS SEPARATION AND DETECTION OF VITAMIN D METABOLITES", which also claims the benefit of and priority to U.S. Provisional Patent Application Ser. No. 61/408,385, entitled "LC-MS SEPARATION AND DETECTION OF VITAMIN D METABOLITES", filed 29 Oct. 2010 with inventors Joseph L. Herman and Dayana Argoti, the entirety of which is incorporated herein by reference. This application also references PCT Application Serial No. PCT/US2011/058430 filed 28 Oct. 2011, entitled "LC-MS CONFIGURATION FOR PURIFICATION AND DETECTION OF ANALYTES HAVING A BROAD RANGE OF HYDROPHOBICITES", which claims the benefit of and priority to U.S. Provisional Patent Application Ser. No. 61/408,266 entitled "LC-MS CONFIGURATION FOR PURIFICATION AND DETECTION OF ANALYTES HAVING A BROAD RANGE OF HYDROPHOBICITES" filed 29 Oct. 2010 with inventors Joseph L. Herman, Robert DeWitte, and Dayana Argoti, the entirety of which is incorporated herein by reference.

BACKGROUND OF THE INVENTION

1. The Field of the Invention

The invention relates to the detection of vitamin D metabolites. In a particular aspect, the invention relates to methods for detecting vitamin D metabolites by liquid chromatography-mass spectrometry with electrospray ionization.

2. The Relevant Technology

Vitamin D is an essential nutrient with important physiological roles in the positive regulation of calcium ($Ca^{2+}$) homeostasis. Vitamin D can be made de novo in the skin by exposure to sunlight or it can be absorbed from the diet. There are two forms of vitamin D; vitamin $D_2$ (ergocalciferol) and vitamin $D_3$ (cholecalciferol). Vitamin $D_3$ is the form synthesized de novo by animals. It is also a common supplement added to milk products and certain food products produced in the United States. Both dietary and intrinsically synthesized vitamin $D_3$ must undergo metabolic activation to generate the bioactive metabolites. In humans, the initial step of vitamin $D_3$ activation occurs primarily in the liver and involves hydroxylation to form the intermediate metabolite 25-hydroxycholecalciferol (calcifediol; $25OHD_3$), which is enzymatically hydroxylated at the 25 position. Calcifediol is the major form of Vitamin $D_3$ in the circulation. Circulating $25OHD_3$ is then converted by the kidney to form 1,25-dihydroxyvitamin $D_3$ (calcitriol; $1,25(OH)_2D_3$), which is generally believed to be the metabolite of Vitamin $D_3$ with the highest biological activity.

Vitamin $D_2$ is derived from fungal and plant sources. Many over-the-counter dietary supplements contain ergocalciferol (vitamin $D_2$) rather than cholecalciferol (vitamin $D_3$). Drisdol, the only high-potency prescription form of vitamin D available in the United States, is formulated with ergocalciferol. Vitamin $D_2$ undergoes a similar pathway of metabolic activation in humans as vitamin $D_3$, forming the metabolites $25OHD_2$ and $1,25(OH)_2D_2$. Vitamin $D_2$ and vitamin $D_3$ have long been assumed to be biologically equivalent in humans, however recent reports suggest that there may be differences in the bioactivity and bioavailability of these two forms of vitamin D.

Measurement of vitamin D, the inactive vitamin D precursor, is rare in clinical settings and has little diagnostic value. Rather, serum levels of 25-hydroxyvitamin $D_3$ and 25-hydroxyvitamin $D_2$ (total 25-hydroxyvitamin D; "25OHD") are useful indices of vitamin D nutritional status and the efficacy of certain vitamin D analogs. Therefore, the measurement of 25OHD is commonly used in the diagnosis and management of disorders of calcium metabolism. In this respect, low levels of 25OHD are indicative of vitamin D deficiency associated with diseases such as hypocalcemia, hypophosphatemia, secondary hyperparathyroidism, elevated alkaline phosphatase, osteomalacia in adults and rickets in children. In patients suspected of vitamin D intoxication, elevated levels of 25OHD distinguishes this disorder from other disorders that cause hypercalcemia.

Detection of vitamin D metabolites has been accomplished by radioimmunoassay with antibodies co-specific for $25OHD_2$ and $25OHD_3$. Because the current immunologically-based assays are not as sensitive and do not separately resolve $25OHD_2$ and $25OHD_3$, the source of any nutritional deficiency of vitamin D cannot be determined without resorting to other tests. More recently, methods for detecting $25OHD_2$ and $25OHD_3$ using mass spectrometry have been reported.

For example, U.S. Pat. No. 7,700,365 (Singh et al.) teaches use of atmospheric pressure chemical ionization (APCI) in the positive ion mode to generate precursor positive ions. In the methods described, the precursor ions of $25OHD_2$ and $25OHD_3$ produce product ions that reflect the loss of water from the sample, Singh et al. teaches ion pair transitions for $25OHD_2$ of 413.0 and 395.3 and for $25OHD_3$ of 401.4 and 383.3.

Similarly, U.S. Pat. No. 7,745,226 (Clarke et al.) discloses APCI and mass spectrometry to determine levels of $25OHD_2$ and $25OHD_3$ using water loss transition ions. According to Clarke et al., the first quadrupole of the mass spectrometer (Q1) selected ions with Da/e (which is equivalent to m/z) ratio of 395.30 ($25OHD_2$) and 383.16 ($25OHD_3$), which were allowed to pass into the collision chamber (Q2). Fragments ions with a Da/e ratio of about 211.35 ($25OHD_3$) and about 179.1, 209.2 and 251.30 ($25OHD_2$) were detected.

Saenger et al. (*Am J Clin Pathol* 125: 914-920, 2006) used electrospray ionization (ESI) in the positive mode and reported the following transitions: 401.15>365.25 ($25OHD_3$) and 413.15>355.20 ($25OHD_2$). No further fragments were disclosed. Capote et al. (*Rapid Commun. Mass Spectrom.* 21: 1745-1754, 2007) used a water-loss precursor ion of $25OHD_3$ (Da/e of about 383) which generated fragments of about 109, 159 and 365, and a precursor ion (m/z of about 413) for $25OHD_2$ with fragments of 93 and 395. Capote et al. specifically teach that $25OHD_2$ "does not undergo fragmentation" of the protonated molecular ion and the product ions (fragments) were "obtained by loss of a water molecule."

U.S. Pat. Pub. No. 2011/0195513 (Calton et al.) discloses a method for preparing samples for detection and quantitation of vitamin D analogs. According to the method, a sample (e.g., human blood serum) is provided and a multiple charge cationic agent (e.g., a divalent cation such as zinc sulfate) is added to it. According to Calton et al., the multiple charge cationic agent removes or facilitates the removal of non-vitamin D compositions from the sample upon centrifugation. After centrifugation, the supernatant is collected, cleaned up with a preparatory medium, eluted, dried down, and resuspended in an appropriate solvent (e.g., methanol/water).

The sample can be further separated and treated for detection and quantitation of vitamin D analogs, if present, by a number of separation methods that include solid phase extraction, liquid/liquid extraction, and protein precipitation. In the solid phase extraction example, the resuspended sample may be loaded on a suitable HPLC column and eluted with the gradient of two solutions: Solution A (2 mM ammonium acetate, 0.1% formic acid, water) and Solution B (2 mM ammonium acetate, 0.1% formic acid, methanol). According to Calton et al., eluted vitamin D analogs may be detected by mass spectrometry; however, few details regarding the identification of suitable precursor ions or fragment ions are provided.

BRIEF SUMMARY

The present invention relates to systems, kits, and methods for quantitation of metabolites of vitamin D by liquid chromatography-mass spectrometry (LC-MS). The systems, kits, and methods described herein stabilize and/or promote the formation of the protonated molecular ion ([M+H]+) for the vitamin D metabolites in the ionization source (e.g., electrospray ionization ("ESI")). Formation of the protonated molecular ion does not involve loss of a water molecule from the parent molecule. Subsequent fragmentation of the [M+H]+ ion yields novel product ions that are specific to each molecular ion and that likewise do not reflect the loss of water in their formation. Because vitamin D metabolites do not have readily ionizable groups, it is surprising and unexpected that protonated vitamin D metabolite ions were observed using the techniques described herein. Moreover, formation of the [M+H]+ ion in the ESI source increases sensitivity approximately ten-fold when compared to atmospheric pressure chemical ionization (APCI). The systems, kits, and methods described herein provide for no compromise in specificity and for a significant increase in sensitivity relative to previously described methods.

In one embodiment, a method for detecting and/or quantifying at least one vitamin D metabolite in a biological sample by liquid chromatography-mass spectrometry is disclosed. The method includes (1) purifying 25-hydroxyvitamin $D_3$, if present in the biological sample, by liquid chromatography using a mobile phase buffer containing an additive capable of stabilizing and/or promoting formation of a 25-hydroxyvitamin $D_3$ ion and (2) ionizing the 25-hydroxyvitamin $D_3$ in a mass spectrometer by electrospray ionization to produce a protonated 25-hydroxyvitamin $D_3$ precursor ion having a mass/charge ratio (Da/e) of about 401.2. The method further includes (3) fragmenting the protonated 25-hydroxyvitamin $D_3$ precursor ion to produce a 25-hydroxyvitamin $D_3$ product ion, wherein at least one product ion has a Da/e of about 159.1, 131.1, 105.1, or 91.1, and (4) detecting a presence or quantity of at least one of a 25-hydroxyvitamin $D_3$ precursor ion or a product ion, wherein the presence or quantity of the detected ion is related to the presence or quantity of 25-hydroxyvitamin $D_3$ in the biological sample.

In one embodiment, the present method further includes purifying, ionizing, fragmenting, and detecting 25-hydroxyvitamin $D_2$ in the biological sample. In one embodiment, the present method further includes purifying, ionizing, fragmenting, and detecting one or more vitamin D metabolites selected from the group consisting of 25-hydroxyvitamin $D_2$, 1,25-dihydroxyvitamin $D_3$, 24,25-dihydroxyvitamin $D_3$, 1,25-dihydroxyvitamin $D_2$, and 24,25-dihydroxyvitamin $D_2$.

In another embodiment, the present invention discloses a method for detecting and/or quantifying at least one vitamin D metabolite including 25-hydroxyvitamin $D_3$ and 25-hydroxyvitamin $D_2$ in a biological sample by liquid chromatography-mass spectrometry. The method includes (1) purifying 25-hydroxyvitamin $D_3$ and 25-hydroxyvitamin $D_2$, if present in the biological sample, by liquid chromatography using a mobile phase buffer containing an additive capable of stabilizing and/or promoting formation of protonated ions specific to each of 25-hydroxyvitamin $D_3$ and 25-hydroxyvitamin $D_2$ and (2) ionizing the 25-hydroxyvitamin $D_3$ and 25-hydroxyvitamin $D_2$ in a mass spectrometer by electrospray ionization to produce protonated precursor ions specific to each of 25-hydroxyvitamin $D_3$ and 25-hydroxyvitamin $D_2$, wherein the 25-hydroxyvitamin $D_3$ precursor ion has a mass/charge ratio (Da/e) of about 401.2 and the 25-hydroxyvitamin $D_2$ precursor ion has a Da/e of about 413.2. The present method further includes (3) fragmenting the isolated precursor ions to produce at least one product ion specific to each of 25-hydroxyvitamin $D_3$ and 25-hydroxyvitamin $D_2$, wherein at least one 25-hydroxyvitamin $D_3$ product ion has a Da/e of about 159.1, 131.1, 105.1, or 91.1 and at least one 25-hydroxyvitamin $D_2$ product ion has a Da/e of about 131.1, 107.1, 105.1, or 91.1, and (4) detecting and/or quantifying a presence or an amount of at least one precursor ion or product ion specific to each of 25-hydroxyvitamin $D_3$ and 25-hydroxyvitamin $D_2$, wherein the presence or quantity of the detected ions is related to the presence or quantity of 25-hydroxyvitamin $D_3$ and 25-hydroxyvitamin $D_2$ in the biological sample.

In yet another embodiment, the present invention includes a system for mass spectrometry of a biological sample containing at least one vitamin D metabolite. The system includes a liquid chromatography system including at least one liquid chromatography column capable of effecting separation of 25-hydroxyvitamin $D_3$ and/or 25-hydroxyvitamin $D_2$ from a biological matrix, reagents for purifying 25-hydroxyvitamin $D_3$ and/or 25-hydroxyvitamin $D_2$ from the biological matrix by liquid chromatography and for analyzing the vitamin D metabolite using a mass spectrometer, wherein the reagents include at least one liquid chromatography buffer that includes a source of ammonium ions, and a mass spectrometer capable of ionizing, fragmenting, and detecting one or more precursor ions or product ions specific to 25-hydroxyvitamin $D_3$ and 25-hydroxyvitamin $D_2$.

Using the system described herein, the 25-hydroxyvitamin $D_3$ precursor ion has a mass-to-charge ratio (Da/e) of about 401.2 and at least one product ion having a Da/e of about 159.1, 131.1, 105.1, or 91.1. Using the system described herein, the 25-hydroxyvitamin $D_2$ precursor ion has a Da/e of about 413.2 and at least one product ion having a Da/e of about 131.1, 107.1, 105.1, or 91.1.

In still yet another embodiment, the present invention includes a kit for mass spectrometry of a sample containing at least one vitamin D metabolite. The kit includes reagents for purifying 25-hydroxyvitamin $D_3$ and/or 25-hydroxyvitamin $D_2$ from a biological matrix by liquid chromatography and for analyzing the vitamin D metabolite using a mass spectrometer, and a protocol for analyzing at least one vitamin D metabolite using a mass spectrometer, wherein the protocol includes instructions for detecting one or more precursor ions or product ions specific to 25-hydroxyvitamin $D_3$ and 25-hydroxyvitamin $D_2$.

Using the protocol included in the kit, precursor ions and product ions specific to each of 25-hydroxyvitamin $D_3$ and 25-hydroxyvitamin $D_2$ may be generated and detected. The 25-hydroxyvitamin $D_3$ precursor ion has a mass-to-charge ratio (Da/e) of about 401.2 and at least one product ion having a Da/e of about 159.1, 131.1, 105.1, or 91.1; the 25-hydroxyvitamin $D_2$ precursor ion has a Da/e of about 413.2 and at least one product ion having a Da/e of about 131.1, 107.1, 105.1, or 91.1.

In one embodiment, the kit further includes at least one liquid chromatography column capable of effecting separation of at least one vitamin D metabolite from a biological matrix, at least one liquid chromatography buffer solution containing a source of ammonium ions, and at least one internal standard for tracking at least one of separation, ionization, fragmentation, or detection of the at least one vitamin D metabolite.

These and other objects and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and are therefore not to be considered limiting of its scope. The invention will be described and explained with additional specificity and detail through the use of the accompanying drawings in which:

FIG. 6 depicts an MS/MS product ion spectrum of Da/e 407 for hexadeuterated 25-hydroxy Vitamin $D_3$ ($d_6$-25-OH $D_3$).

FIG. 9A depicts an ESI full scan spectrum of the molecular ion region for 25-OH $D_2$ using ammonium formate;

FIG. 9B depicts an atmospheric pressure chemical ionization ("APCI") full scan spectrum of the molecular ion region for 25-OH $D_2$ using ammonium formate;

FIG. 12A depicts the SRM signal from 25-OH $D_3$ using ESI to produce the [M+H]+ molecular ion; and FIG. 12B depicts the SRM signal from 25-OH $D_3$ using APCI to produce the [M+H–$H_2O$]+ water loss ion.

DETAILED DESCRIPTION

I. Introduction and Definitions

Figure 1:
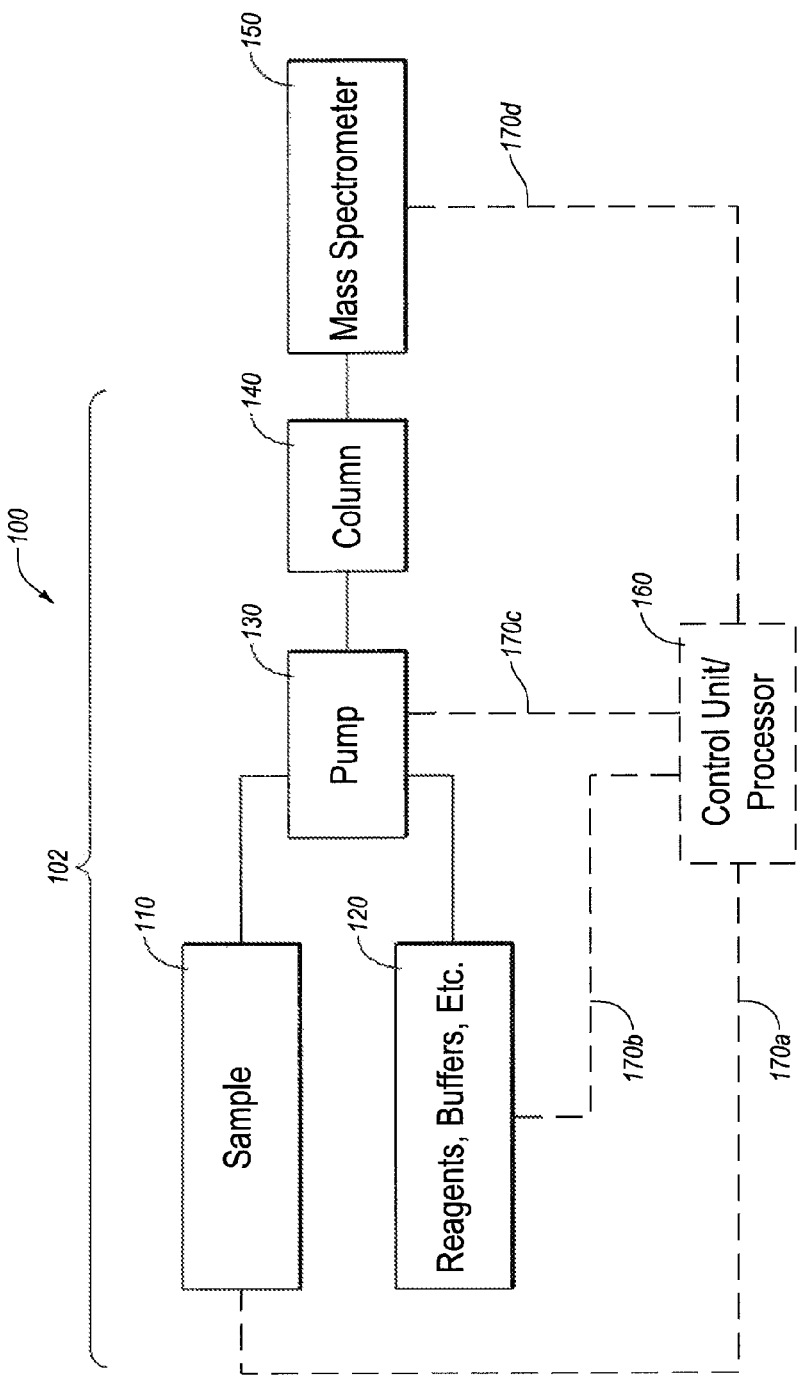
FIG. 1 is a block diagram schematically illustrating a system for separation and analysis of vitamin D metabolites.

The present invention relates to systems, kits, and methods for quantitation of metabolites of vitamin D by liquid chromatography-mass spectrometry (LC-MS). The systems, kits, and methods described herein stabilize and/or promote the formation of the protonated molecular ion ([M+H]+) for the vitamin D metabolites in the ionization source (e.g., electrospray ionization ("ESI") or atmospheric pressure chemical ionization ("APCI")). Formation of the protonated molecular ion does not involve loss of a water molecule from the parent molecule. Subsequent fragmentation of the [M+H]+ ion yields novel product ions that are specific to each molecular ion and that likewise do not reflect the loss of water in their formation. Because vitamin D metabolites do not have readily ionizable groups, it is surprising and unexpected that protonated vitamin D metabolite ions were observed using the techniques described herein. Moreover, formation of the [M+H]+ ion in the ESI source increases sensitivity approximately ten-fold when compared to APCI. The systems, kits, and methods described herein provide for no compromise in specificity and for a significant increase in sensitivity relative to previously described methods.

Steroid hormones and related endogenous compounds, such as Vitamin D and its metabolites, pose challenging analytical problems to analysis by LC-MS technology because the compounds do not contain readily ionizable functional groups. As a result, it is common for the parent molecules of such compounds that contain hydroxyl groups to ionize in the LC-MS environment by losing one equivalent of water. Because there are multiple routes for water loss available to related parent compounds (e.g., vitamin D metabolites), such water loss leads to a compromise in specificity of the analytical method. By stabilizing and promoting the formation of the [M+H]+ molecular ion, the present invention provides a precursor ion that is unique to each vitamin D metabolite and a set of product ions that is unique and traceable to each vitamin D metabolite, wherein the product ions are formed by fragmentation of the precursor protonated molecular ions without water loss.

While the addition of volatile organic buffering reagents (such as ammonium formate) to liquid chromatography mobile phases for LC-MS has been shown to produce a relative increase the abundance of [M+H]+ ions for certain compounds where [M+H]+ has been observed, it has not previously been shown to generate [M+H]+ ions where none had been observed. In some situations, one might observe formation of [M+$NH_4$]+ ions rather than or in addition to the [M+H]+ ions.

However, when this technique was applied to vitamin D metabolites, the inventors discovered that the addition of ammonium formate promoted the formation and stabilized the formation of the protonated molecular ion [M+H]+ in the ESI source, and increased the sensitivity approximately ten-fold when compared to the traditional APCI methodology (with or without ammonium formate). The measured increase in sensitivity is different for vitamin $D_2$ vs. vitamin $D_3$, and also may be dependent on specific instrument settings and designs as well as specific SRM transitions.

Typically, for vitamin D and its metabolites, one uses the APCI ionization technique, rather than ESI because it has been shown to be more sensitive. Also typical for vitamin D and its metabolites, one measures the loss of water [M+H–

$H_2O]+$ ion rather than the $[M+H]+$ ion. This is because very little if any $[M+H]+$ ion is formed using conventional methods. By contrast, the inventors discovered that when a source of ammonium ions was added to the mobile phase, the vitamin D analogs not only formed $[M+H]+$ ions but the abundance of product ion transitions was ten times greater than when $[M+H]+-H_2O$ ions are generated. The practical benefits of this include more sensitive detection (so that smaller sample sizes can be used and/or better signal to noise ratios can be achieved), and more specific detection, so that quantitation experiments of vitamin D metabolites are not confused one with the other.

As used herein, the term "vitamin D metabolite" refers to any vitamin D analog or any chemical species related to vitamin D. Vitamin D metabolites may include analogs of, or a chemical species related to, vitamin $D_2$ or vitamin $D_3$. Vitamin D metabolites may be found in the circulation of an animal and/or may be generated by a biological organism, such as an animal, or by biotransformation of vitamin $D_2$ or vitamin $D_3$. Vitamin D metabolites may be metabolites of naturally occurring forms of vitamin D or may be metabolites of synthetic vitamin D analogs. In certain embodiments a vitamin D metabolite is one or more compounds selected from the group consisting of 25-hydroxyvitamin $D_3$, 25-hydroxyvitamin $D_2$, 1,25-dihydroxyvitamin $D_3$, 24,25-dihydroxyvitamin $D_3$, 1,25-dihydroxyvitamin $D_2$, and 24,25-dihydroxyvitamin $D_2$.

Purification in the context of the methods of the invention does not refer to removing all materials from the sample other than the analyte(s) of interest. Instead, in one aspect, purification may refer to a procedure that enriches the amount of one or more analytes of interest relative to one or more other components of the sample. In another aspect, purification can be used to remove one or more interfering substances, e.g., one or more substances that would interfere with detection of an analyte ion by mass spectrometry.

As used herein, "sample" refers to any fluid or liquefied sample and "biological sample" refers to any sample from a biological source. As used herein, "body fluid" means any fluid that can be isolated from the body of a human or animal. For example, "body fluid" may include blood, plasma, serum, milk, bile, saliva, urine, tears, perspiration, and the like. Samples may further include those from dietary, industrial and environmental sources.

As used herein, "kit" refers to two or more components comprising reagents, devices, calibrators, controls, standards, or any combination thereof, for performance of a common method, regardless of whether the two or more components are provided within a single package or multiple packages.

As used herein, "chromatography" refers to a process in which a chemical mixture carried by a liquid, gas or supercritical fluid is separated into components as a result of differential distribution of the solutes as they flow around or over a stationary or chemically interact with a liquid or solid phase.

As used herein, "liquid chromatography" (LC) means a process of selective retention of one or more components of a fluid solution as the fluid uniformly percolates through a column of a finely divided substance, or through capillary passageways. The retention results from the distribution of the components of the mixture between one or more stationary phases and the bulk fluid, (i.e., mobile phase), as this fluid moves relative to the stationary phase(s). "Liquid chromatography" includes, without limitation, reverse phase liquid chromatography (RPLC), high performance liquid chromatography (HPLC), ultra high performance liquid chromatography (UHPLC), supercritical fluid chromatography (SFC) and ion chromatography.

As used herein, the term "HPLC" or "high performance liquid chromatography" refers to liquid chromatography in which the degree of separation is increased by forcing the mobile phase under pressure through a stationary phase, typically a densely packed column.

As used herein, the term "UHPLC" or "ultra high performance liquid chromatography" refers to a liquid chromatography technique similar to HPLC except the operating pressures are higher than HPLC (e.g., about 100 MPa vs. about 40 MPa), the columns are typically smaller in diameter, the particles of packing material are generally smaller, and resolution can be greater.

As used herein, "mass spectrometry" (MS) refers to an analytical technique to filter, detect, identify and/or measure compounds by their mass to charge ratio, of "Da/e." MS technology generally includes (1) ionizing the compounds and potentially fragmenting the compounds; and (2) detecting the molecular weight of the charged compound and/or fragment ion and calculating a mass-to-charge ratio (Da/e). The compound may be ionized and detected by any suitable means. A "mass spectrometer" generally includes an ionizer and an ion detector.

The term "ESI" or "electrospray ionization" refers to a technique used in mass spectrometry to produce ions. It is especially useful in producing ions from macromolecules because it overcomes the propensity of these molecules to fragment when ionized. In ESI a stream of fluid is ejected from a nozzle, cone or other directive device which may or may not be electrically charged. Molecular ions (e.g., $[M+H]+$) may be formed in the liquid phase or as a function of the chemical processes occurring during evaporation of the solvent shell around the analyte or in the gas phase.

The term "ionization" as used herein refers to the process of generating an analyte ion having a net electrical charge. Negative ions are those having a net negative charge, while positive ions are those having a net positive charge.

The term "operating in negative ion mode" refers to those mass spectrometry methods where negative ions are detected. Similarly, "operating in positive ion mode" refers to those mass spectrometry methods where positive ions are detected.

The term "desorption" as used herein refers to the removal of an analyte from a surface and/or the entry of an analyte into a gaseous phase.

The term "about" as used herein in reference to quantitative measurements, refers to the indicated value plus or minus 10%.

II. Systems for Mass Spectrometry of a Biological Sample Containing at Least One Vitamin D Metabolite Referring now to FIG. 1, a system 100 for mass spectrometry of a biological sample containing at least one vitamin D metabolite is schematically illustrated. The system 100 includes a liquid chromatography system 102 capable of effecting separation of 25-hydroxyvitamin $D_3$ and 25-hydroxyvitamin $D_2$ from a biological matrix and a mass spectrometer 150 capable of ionizing, fragmenting, and detecting one or more precursor ions or product ions specific to 25-hydroxyvitamin $D_3$ and 25-hydroxyvitamin $D_2$.

The liquid chromatography system 102 illustrated in FIG. 1 includes a sample 110, reagents 120 for purifying 25-hydroxyvitamin $D_3$ and 25-hydroxyvitamin $D_2$ from the biological matrix by liquid chromatography and for analyzing the vitamin D metabolite using a mass spectrometer, wherein the reagents include at least one liquid chromatography buffer that includes a source of ammonium ions, a fluid handling pump, and a column 140 capable of effecting separation of 25-hydroxyvitamin $D_3$ and 25-hydroxyvitamin $D_2$ from a biological matrix. As illustrated in FIG. 1, the system 100 further includes a control unit 160 that can be linked to various components of the system 100 through linkages 170a-170d. For example, the control unit 160 can be linked to the sample 110 to control sample application, the reagents 120 to control the application of various reagents, the pump 130 to control fluid handling, flow rates, etc, and to the mass spectrometer 150. In the illustrated embodiment, the control unit 160 can also serve as a data processing unit to, for example, process data from the mass spectrometer 150.

Suitable test samples include any sample that might contain the analyte of interest and/or one or more metabolites or precursors thereof. For example, samples obtained during the manufacture of an analyte can be analyzed to determine the composition and yield of the manufacturing process. In certain embodiments, a sample is a biological sample; that is, a sample obtained from any biological source, such as an animal, a cell culture, an organ culture, etc. Particularly preferred are samples obtained from a human or animal, such as a blood, plasma, deproteinated plasma, serum, milk, muscle, urine, saliva, tear, cerebrospinal fluid, or other tissue sample. Such samples may be obtained, for example, from a patient; that is, a living person presenting themselves in a clinical setting for diagnosis, prognosis, or treatment of a disease or condition.

Samples may be processed or purified to obtain preparations that are suitable for the desired type of chromatography and/or for analysis by mass spectrometry. Various procedures may be used for this purpose depending on the type sample or the type of chromatography. Examples include filtration, extraction, precipitation, centrifugation, dilution, combinations thereof and the like. Protein precipitation is one example method of preparing a liquid biological sample, such as serum or plasma, for chromatography. In one embodiment, a volume of the liquid sample is added to a sufficient volume of methanol to cause precipitation of most of the proteins in the sample while vitamin D metabolites are fully soluble in the resulting supernatant. The samples can then be centrifuged to separate the liquid supernatant from the pellet. The resultant supernatants can then be applied to liquid chromatography and mass spectrometry analysis. In some embodiments, the system 100 includes a quality control standard (e.g., hexadeuterated 25-OH $D_3$, $d_6$-25-OH $D_3$) that can be used to track at least one of the handling, separation, ionization, fragmentation, or detection of the at least one vitamin D metabolite.

The sample, or the processed sample, may be purified prior to analysis by mass spectrometry. Such purification, or sample clean-up, refers to a procedure that enriches of one or more analytes of interest relative to one or more other components of the sample. Typically, one or more methods including, without limitation, liquid chromatography, HPLC, UHPLC, precipitation, dialysis, affinity capture, electrophoresis, or other suitable methods known in the art, are used for the purification. These procedures may be performed "on-line" in an automated or semi-automated system directly connected to a mass spectrometer or performed "off-line" using a separate system or manual method.

Various methods have been described involving the use of HPLC for sample clean-up prior to mass spectrometry analysis. See, e.g., Taylor et al., Therapeutic Drug Monitoring 22:608-12 (2000) (manual precipitation of blood samples, followed by manual C18 solid phase extraction, injection into an HPLC for chromatography on a C18 analytical column, and MS/MS analysis); and Salm et al., Clin. Therapeutics 22 Supl. B:B71-B85 (2000) (manual precipitation of blood samples, followed by manual C18 solid phase extraction, injection into an HPLC for chromatography on a C18 analytical column, and MS/MS analysis). One of skill in the art can select HPLC instruments and columns that are suitable for use in the invention. The chromatographic column typically includes a medium (i.e., a packing material) to facilitate separation of chemical moieties (i.e., fractionation). The medium may include minute particles. The particles may include a bonded surface that interacts with the various chemical moieties to facilitate separation of the chemical moieties such as vitamin D metabolites. One suitable bonded surface is a hydrophobic bonded surface such as an alkyl bonded surface. Alkyl bonded surfaces may include C-4, C-8, or C-18 bonded alkyl groups, preferably C-18 bonded groups. The chromatographic column includes an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used wherein a test sample may applied to a first column (e.g., a clean-up column such as a Cyclone P column or the like) at the inlet port, eluted with a solvent or solvent mixture onto a second column, for example, an analytical HPLC column such as a Hypersil Gold PFP™, Accucore PFP™ column (Thermo Fisher Scientific) or Halo™ column (Advanced Materials Technologies) or the like, and eluted with a solvent or solvent mixture from the second column to the outlet port. Different solvent modes may be selected for eluting the analytes. For example, liquid chromatography may be performed using a gradient mode, an isocratic mode, or a polytyptic (i.e. mixed) mode.

Recently, high turbulence liquid chromatography ("HTLC"), also called high throughput liquid chromatography, has been applied for sample preparation prior to analysis by mass spectrometry. See, e.g., Zimmer et al., J. Chromatogr. A 854:23-35 (1999); see also, U.S. Pat. Nos. 5,968,367; 5,919,368; 5,795,469; and 5,772,874, each of which is hereby incorporated by reference in its entirety. Traditional HPLC analysis relies on column packings in which laminar flow of the sample through the column is the basis for separation of the analyte of interest from the test sample. The skilled artisan will understand that separation in such columns is a diffusional process. In contrast, it is believed that turbulent flow, such as that provided by HTLC columns and methods, may enhance the rate of mass transfer, improving the separation characteristics provided. In some embodiments, high turbulence liquid chromatography (HTLC), alone or in combination with one or more purification methods, may be used to purify the vitamin D metabolite of interest. In such embodiments samples may be extracted using an HTLC extraction cartridge which captures the analyte, then eluted and chromatographed on a second HPLC column prior to ionization. Because the steps involved in these two HTLC procedures can be linked in an automated fashion, the requirement for operator involvement during the purification of the analyte can be minimized.

In general, one or more molecules of interest, such a vitamin D metabolites, are ionized and the ions are subsequently introduced into a mass spectrographic instrument where, due to a combination of magnetic and electric fields, the ions follow a path in space that is dependent upon mass ("m" or "Da") and charge ("z" or "e").

The mass spectrometer 150 will include an ion source for ionizing the fractionated sample and creating charged molecules for further analysis. For example ionization of the sample may be performed by electrospray ionization (ESI).

Other ionization techniques include, but are not limited to, atmospheric pressure chemical ionization (ACPI), photoionization, electron impact ionization, chemical ionization, fast atom bombardment (FAB)/liquid secondary ion mass spectrometry (LSIMS), matrix assisted laser desorption ionization (MALDI), field ionization, field desorption, thermospray/plasmaspray ionization, and particle beam ionization. The skilled artisan will understand that the choice of ionization method can be determined based on the analyte to be measured, type of sample, the type of detector, the choice of positive versus negative mode, etc.

After the sample has been ionized, the positively charged or negatively charged ions thereby created may be analyzed to determine a mass-to-charge ratio (i.e., Da/e). Suitable analyzers for determining mass-to-charge ratios include quadrupole analyzers, ion traps analyzers, and time-of-flight analyzers. The ions may be detected by using several detection modes. For example, selected ions may be detected (i.e., using a selective ion monitoring mode (SIM)), or alternatively, ions may be detected using selected reaction monitoring (SRM) or multiple reaction monitoring (MRM) (MRM and SRM are essentially the same). Ions can also be detected by scanning the mass spectrometers to detect all the precursor ions simultaneously or all the products ions of a specific precursor ion simultaneously or both.

In one embodiment, the mass-to-charge ratio is determined using a quadrupole analyzer. For example, in a "quadrupole" or "quadrupole ion trap" instrument, ions in an oscillating radio frequency field experience a force proportional to the DC potential applied between electrodes, the amplitude of the radio frequency ("RF") signal, and Da/e. The voltage and amplitude can be selected so that only ions having a particular Da/e travel the length of the quadrupole, while all other ions are deflected. Thus, quadrupole instruments can act as a "mass filter," a "mass separator" or an ion lens for the ions injected into the instrument.

One can often enhance the resolution of the MS technique by employing "tandem mass spectrometry" or "MS/MS" for example via use of a triple quadrupole mass spectrometer. In this technique, a first, or parent, or precursor, ion generated from a molecule of interest can be filtered in an MS instrument, and these precursor ions subsequently fragmented to yield one or more second, or product, or fragment, ions that are then analyzed in a second MS procedure. By careful selection of precursor ions, only ions produced by certain analytes are passed to the fragmentation chamber, where collision with atoms of an inert gas is used to produce these product ions. Because both the precursor and product ions are produced in a reproducible fashion under a given set of ionization/fragmentation conditions, the MS/MS technique can provide an extremely powerful analytical tool. For example, the combination of filtration/fragmentation can be used to eliminate interfering substances, and can be particularly useful in complex samples, such as biological samples.

For example, a flow of liquid solvent from a chromatographic column, possibly containing one or more vitamin D metabolites, enters the heated nebulizer interface of a LC-MS/MS analyzer and the solvent/analyte mixture is converted to vapor in the heated tubing of the interface. Without being tied to one theory, it is believed that the vitamin D metabolites that are ionized in the mobile phase are ejected into the gas phase by nebulization in the ESI source or by reactions between the neutral metabolites and ammonium ions as the metabolites enter the gas phase.

The ions pass through the orifice of the instrument and enter the first quadrupole. Quadrupoles 1 and 3 (Q1 and Q3) are mass filters, allowing selection of ions based on their mass to charge ratio (Da/e). Quadrupole 2 (Q2) is RF-only (non-filtering) and serves as the collision cell, where ions are fragmented. The first quadrupole of the mass spectrometer (Q1) selects for molecules with the mass to charge ratios of [M+H]+ ions specific to each vitamin D metabolite to be analyzed. Ions with the correct Da/e ratios of the vitamin D metabolites are allowed to pass into the collision chamber (Q2), while unwanted ions with any other Da/e are ejected from or collide with the sides of the quadrupole and are eliminated. Ions entering Q2 collide with neutral gas molecules (e.g., argon) and fragment. This process is called Collision Activated Dissociation (CAD). The fragment ions generated are passed into quadrupole 3 (Q3), where the fragment ions of the desired vitamin D metabolites are selected while other ions are eliminated. As ions collide with the detector they produce a pulse of electrons that are converted to a digital signal. Other mass spectrometers useful for the present invention include those that generate photons to produce a pulse of electrons.

Figure 4:
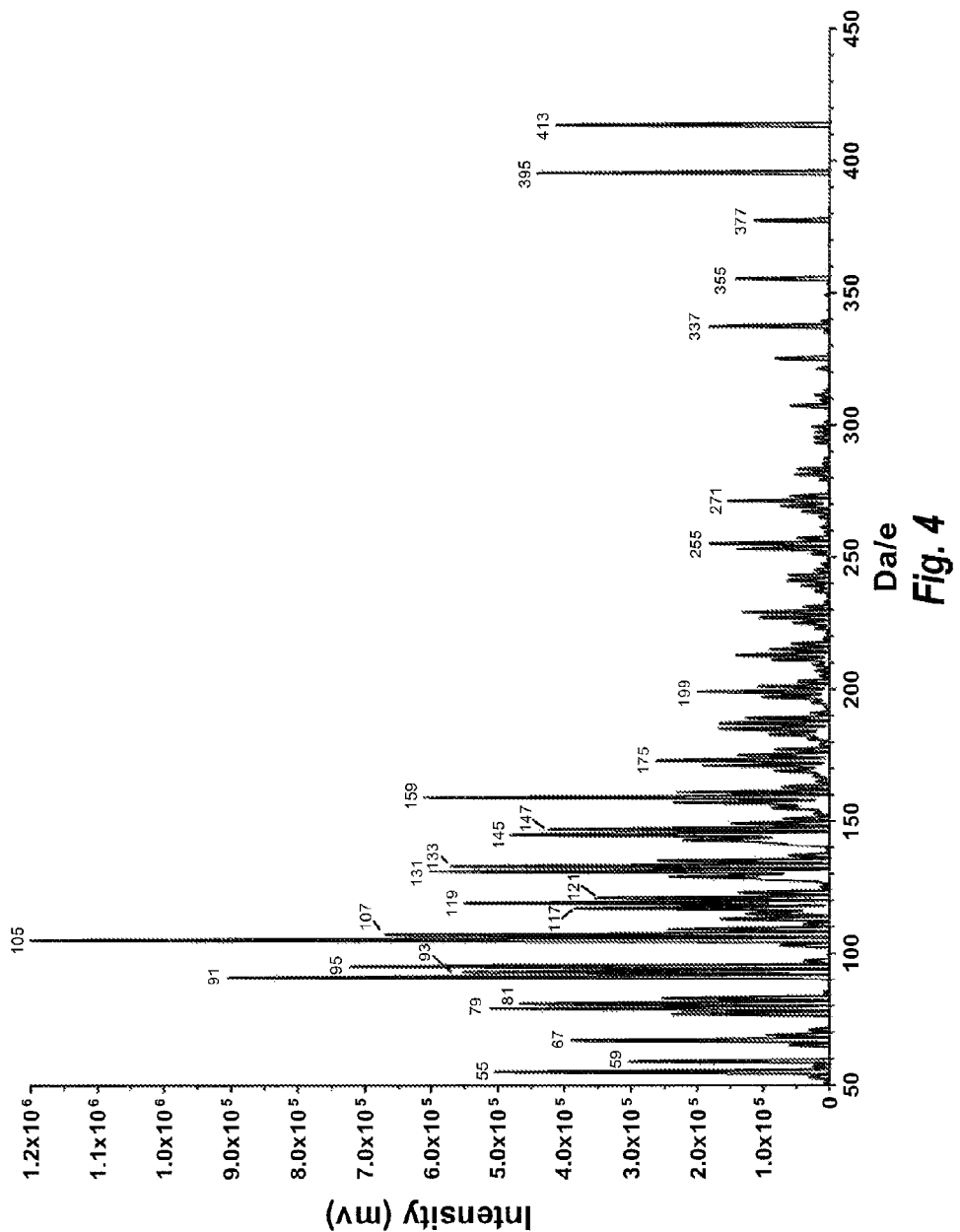
FIG. 4 depicts an MS/MS product ion spectrum of Da/e 413 for 25-hydroxy Vitamin $D_2$.

The mass/charge ratio (Da/e) for the 25-hydroxyvitamin $D_3$ [M+H]+ precursor ion produced using the systems, kits, and methods described herein is about 401.2. As is shown in FIG. 4, many product ion fragments are produced and may vary between LC-MS systems. Typically the most prevalent fragments obtained are identified for determining the presence and/or concentration of the target analyte. For example, the Da/e of the product ions produced from 25-hydroxyvitamen $D_3$ using the system and methods described herein is about 159.1, 131.1, 105.1, or 91.1. The mass/charge ratio (Da/e) for the 25-hydroxyvitamin $D_2$ [M+H]+ precursor ion produced using the systems, kits, and methods described herein is about 413.2 and the Da/e of the prevalent product ions produced as described herein is about 131.1, 107.1, 105.1, or 91.1.

Mass spectrometry instruments can vary slightly in determining the mass of a given analyte. Thus, the term "about" in the context of mass of an ion or the Da/e of an ion refers to +/−0.5 atomic mass units or Daltons (Da). The acquired data is relayed to a computer, which plots voltage versus time. The resulting mass chromatograms are similar to chromatograms generated in traditional HPLC methods. One method of quantifying the results is to determine the areas under the peaks and construct calibration curves by plotting standard concentration versus peak area ratio of analyte/internal standard. Other methods of quantitation as known to those skilled in the art may be used to determine concentration of a target analyte. Concentrations of the vitamin D metabolites may be determined by calculating the area under the peaks in the spectrogram. The concentration of a vitamin D metabolite is typically determined either by comparing the area of the peaks to a calibration curve and/or comparing the ratio of internal standards (e.g., deuterated 25-hydroxyvitamin $D_3$) to test samples.

III. Kits for Mass Spectrometry of a Sample Containing at Least One Vitamin D Metabolite In one embodiment, a kit for mass spectrometry of a sample containing at least one vitamin D metabolite is disclosed. With the kit disclosed herein, a user can analyze a sample and detect and/or quantify at least one vitamin D metabolite (e.g., 25-hydroxyvitamin $D_3$ and 25-hydroxyvitamin $D_2$) in the sample.

In one embodiment, the kit includes reagents for purifying 25-hydroxyvitamin $D_3$ and 25-hydroxyvitamin $D_2$ from a biological matrix by liquid chromatography and for analyzing the vitamin D metabolite using a mass spectrometer, and a protocol for analyzing at least one vitamin D metabolite using a mass spectrometer. In one embodiment, the protocol includes instructions for generating and detecting one or more precursor ions or product ions specific to 25-hydroxyvitamin $D_3$ and 25-hydroxyvitamin $D_2$. For example, the protocol may include instructions relating to sample handling and preparation, liquid chromatography conditions (e.g., flow rates, gradients, columns, temperature, etc.), composition of buffers for LC-MS, mass spectrometer settings (e.g., spray voltage, desolvation temperature, sheath gas pressure, voltage and scan settings for the mass analyzer(s), etc.).

With the kit disclosed herein, a user can analyze a sample and detect and/or quantify a 25-hydroxyvitamin $D_3$ precursor ion having a mass-to-charge ratio (Da/e) of about 401.2 and at least one product ion having a Da/e of about 159.1, 131.1, 105.1, or 91.1 and a 25-hydroxyvitamin $D_2$ precursor ion having a Da/e of about 413.2 and at least one product ion having a Da/e of about 131.1, 107.1, 105.1, or 91.1.

In one embodiment, the kit further includes at least one liquid chromatography column capable of effecting separation of at least one vitamin D metabolite from a biological matrix, at least one liquid chromatography buffer solution containing a source of ammonium ions, at least one internal standard for tracking at least one of separation, ionization, fragmentation, or detection of the at least one vitamin D metabolite.

Chromatographic columns typically include an inlet port for receiving a sample and an outlet port for discharging an effluent that includes the fractionated sample. For example, a test sample may be applied to the column at the inlet port, eluted with a solvent or solvent mixture, and discharged at the outlet port. In another example, more than one column may be used wherein a test sample may be applied to a first column (e.g., a clean-up column) at the inlet port, eluted with a solvent or solvent mixture onto a second column (e.g., an analytical column), and eluted with a solvent or solvent mixture from the second column to the outlet port.

Many types of HPLC and UHPLC columns are commercially available and can be selected based on various criteria known to persons having ordinary skill in the art. For example, commercially available HPLC and UHPLC columns include normal-phase (polar stationary phases and non-polar mobile phases), reverse-phase (the stationary phase is non-polar and the mobile phase is polar), ion-exchange (charged species on the stationary phase and charged species in the mobile phase), fused-core, solid core and affinity chromatography (based on specific interactions in a lock-and-key paradigm between analytes and matrix-bound ligands). In one embodiment, the liquid chromatography is reverse-phase. Suitable reverse phase columns include, but are not limited to, C-4, C-8, C-18, Hypersil Gold PFP™, Accucore PFP™, and the like.

In one embodiment, the at least one liquid chromatography buffer solution containing a source of ammonium ions including ammonium formate and/or ammonium acetate. Preferably, the source of ammonium ions is volatile so that it can be removed by the vacuum in the mass spectrometer, preventing damage from residue. In one embodiment, ammonium formate and/or ammonium acetate may be included in the mobile phase buffer in an amount ranging from about 2 mM to about 10 mM, or about 4 mM to about 8 mM, or about 10 mM. Lower amounts of ammonium formate and/or ammonium acetate may be used for example, as low as about 0.1 mM, but below approximately about 2 mM ionization of the vitamin D metabolites may be sub-optimal. Higher amounts of ammonium formate and/or ammonium acetate may be used for example, as high as about 20 mM to 100 mM. However, staying below approximately 10 mM minimizes the risk of charge-charge repulsion of ammonium ions in solution and/or the gas phase which can produce artifacts and reduce sensitivity.

Ammonium formate and ammonium acetate are acceptable sources of ammonium ions for use in LC-MS. Ammonium formate's pKa is lower than ammonium acetate's and, as such, the analytes of interest will be expected to be more fully ionized in the buffer solution, which may be desirable in some instances. Both ammonium formate and ammonium acetate are acceptable because they are sources of volatile ions and are not expected to interfere with mass spectrometry results. In contrast, ammonium chloride and ammonium citrate, also sources of ammonium ions, are generally considered to be unacceptable for use in LC-MS because the chloride is not volatile and would therefore be expected to foul the mass spectrometer.

In one embodiment, the at least one liquid chromatography buffer solution containing a source of ammonium ions includes an aqueous solution (e.g., water, ammonium formate, and formic acid) or a non-aqueous solution (e.g., methanol, ammonium formate, and formic acid). Other organic phases that can be used include, but are not limited to, acetonitrile, ethanol, isopropanol, and combinations thereof. In another embodiment, both aqueous and non-aqueous buffers can be used. For example, samples can be loaded and washed with aqueous buffer and eluted in an aqueous to non-aqueous gradient or isocratically (e.g., with 100% non-aqueous buffer).

IV. Methods for Detecting and/or Quantifying at Least One Vitamin D Metabolite

Figure 2:
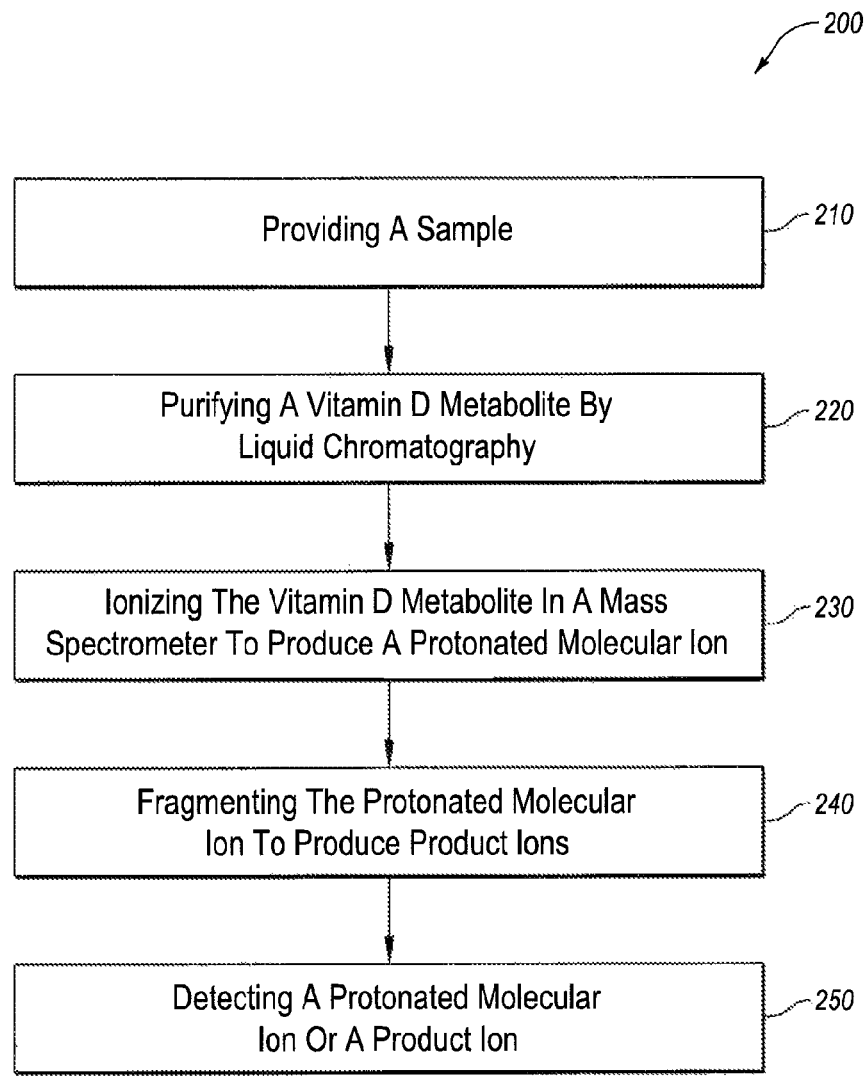
FIG. 2 is a flow diagram illustrating a method for purifying and analyzing vitamin D metabolites.

Referring now to FIG. 2, a method 200 for detecting and/or quantifying at least one vitamin D metabolite in a sample by liquid chromatography-mass spectrometry is illustrated. The illustrated method includes providing a sample (210), purifying at least one vitamin D metabolite, if present in the sample, by liquid chromatography (220), ionizing the at least one vitamin D metabolite in a mass spectrometer by electrospray ionization to produce a protonated precursor ion (230), fragmenting the protonated precursor ion to produce at least one product ion (240), and detecting at least one of a precursor ion or a product ion (250).

Suitable examples of vitamin D metabolites that may be in the sample include, but are not limited to, 25-hydroxyvitamin $D_3$, 25-hydroxyvitamin $D_2$, 1,25-dihydroxyvitamin $D_3$, 24,25-dihydroxyvitamin $D_3$, 1,25-dihydroxyvitamin $D_2$, and 24,25-dihydroxyvitamin $D_2$.

In one embodiment, the liquid chromatography is high-performance liquid chromatography ("HPLC") or ultra high-performance liquid chromatography ("UHPLC").

In one embodiment, the chromatography system can include a sample clean up liquid chromatography column and an analytical liquid chromatography column. For example, the sample clean up column can be a column that is capable of separating small molecules (e.g., vitamin D metabolites) from the macromolecules (e.g., proteins and nucleic acid polymers) in biological matrix. Suitable examples of sample clean up columns include, but are not limited to, Cyclone P (Thermo Fisher Scientific), other TurboFlow® columns (C18 XL, C18 P XL, C8, etc.) (Thermo Fisher Scientific), SPE-Oasis (Waters), Strata-X (Phenomenex), Prospekt (Spark Holland), RAM-Shim-pak (YMC), and the like. The analytical column, for example, can be a column that is capable of collecting the small molecules from the sample clean up column, concentrating them at the head of the column, and separating them chromatographically using a selected elution protocol (e.g., a buffer gradient or isocratic elution). Suitable examples of analytical columns include, but are not limited to, C8, C18, Hypersil Gold PFP analytical column (Thermo Fisher Scientific), Accucore PFP™ (Thermo Fisher Scientific), Zorbax (Agilent Technologies), Xterra, UBondapak, Symmetry, Aquity (Waters), Luna, Jupiter, Synergi (Phenomenex), and the like.

In one embodiment, the chromatography system, including the sample clean up column and the analytical column, is in fluid communication with reagents for purifying at least one vitamin D metabolite from a biological matrix by liquid chromatography and analyzing the vitamin D metabolite by mass spectrometry. The reagents include an aqueous buffer and a non-aqueous buffer that each contain a mobile phase buffer additive capable of stabilizing and/or promoting formation of protonated ions specific to each vitamin D metabolite.

In one embodiment, the additive includes or forms ammonium ions in the mobile phase buffer. In one embodiment, the additive is ammonium formate or ammonium acetate. In one embodiment, the additive is included in the mobile phase buffer in an amount ranging from about 2 mM to about 10 mM, or about 4 mM to about 8 mM, or about 10 mM.

Figure 3:
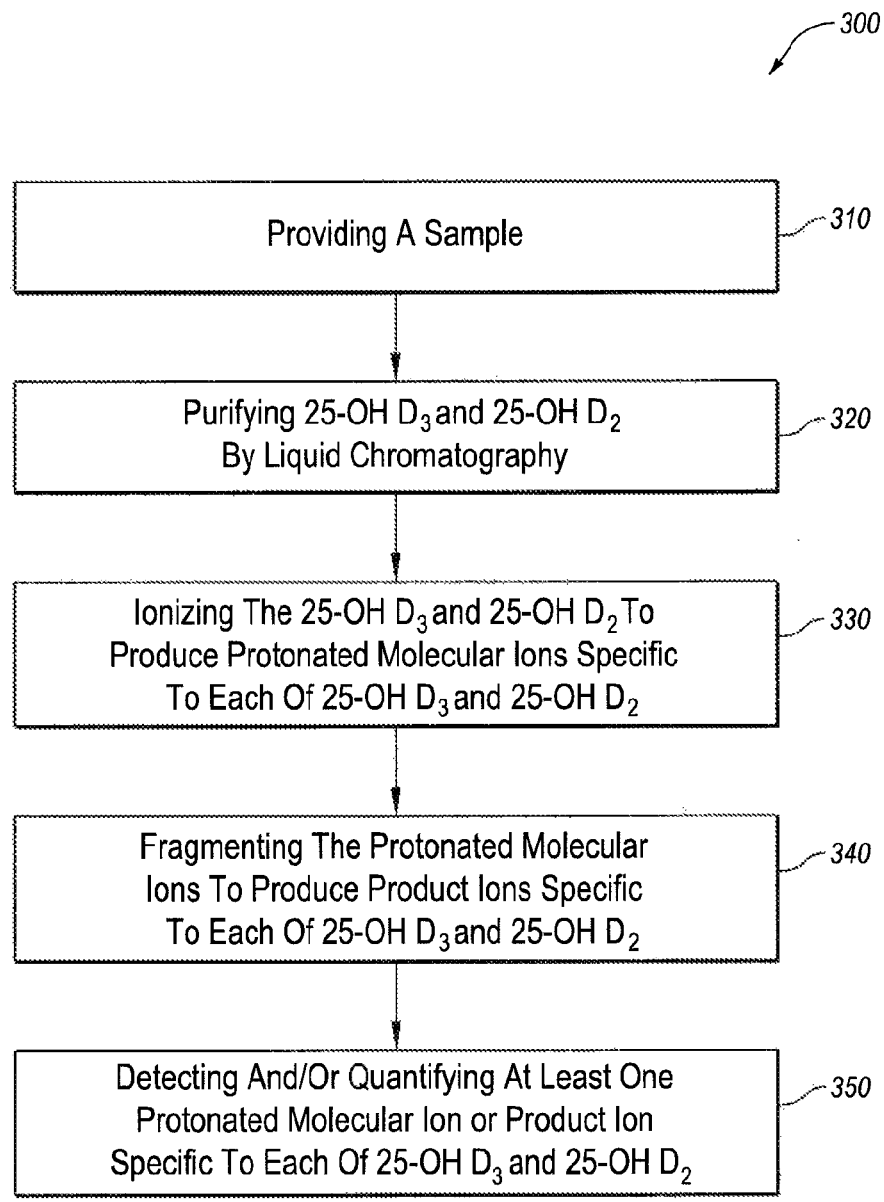
FIG. 3 is a flow diagram illustrating a method for simultaneous separation and analysis of 25-hydroxyvitamin $D_3$ and 25-hydroxyvitamin $D_2$.

Referring now to FIG. 3, a method 300 for detecting and/or quantifying at least one vitamin D metabolite including 25-hydroxyvitamin $D_3$ and 25-hydroxyvitamin $D_2$ by liquid chromatography-mass spectrometry is illustrated. The method 300 includes providing a sample (310). The sample may be from a biological source such as an animal or human, a cell culture, an organ culture, and the like that is likely to contain least one vitamin D metabolite including 25-hydroxyvitamin $D_3$ and 25-hydroxyvitamin $D_2$. Suitable examples of biological samples include, but are not limited to, blood, plasma, deproteinated plasma, serum, milk, muscle, urine, saliva, tear, cerebrospinal fluid, or another tissue sample. Such samples may be obtained, for example, from a patient; that is, a living person presenting themselves in a clinical setting for diagnosis, prognosis, or treatment of a disease or condition.

In some embodiments, a selected subset of biological samples can be augmented with a quality control standard (e.g., $d_6$-25-OH $D_3$) that can be used to track at least one of the handling, separation, ionization, fragmentation, or detection of the at least one vitamin D metabolite. For example, vitamin D and its metabolites are heat- and photo-labile. In order to track proper handling of samples, selected samples can be spiked with a known quantity of a quality control standard. If the samples are properly handled, the known amount of the quality control standard should be detected in analysis.

Suitable examples of samples can also include samples spiked with known amounts of one or more vitamin D metabolites for the purpose of calibrating the LC-MS instrument.

The method 300 further includes purifying 25-hydroxyvitamin $D_3$ and 25-hydroxyvitamin $D_2$, if present in the biological sample, by liquid chromatography (320), ionizing the 25-hydroxyvitamin $D_3$ and 25-hydroxyvitamin $D_2$ in a mass spectrometer by electrospray ionization to produce protonated precursor ions specific to each of 25-hydroxyvitamin $D_3$ and 25-hydroxyvitamin $D_2$ (330), fragmenting the isolated precursor ions to produce at least one product ion specific to each of 25-hydroxyvitamin $D_3$ and 25-hydroxyvitamin $D_2$ (340), and detecting and/or quantifying a presence or an amount of at least one precursor ion or product ion specific to each of 25-hydroxyvitamin $D_3$ and 25-hydroxyvitamin $D_2$, wherein the presence or quantity of the detected ions is related to the presence or quantity of 25-hydroxyvitamin $D_3$ and 25-hydroxyvitamin $D_2$ in the biological sample (350).

The mass/charge ratio (Da/e) for the 25-hydroxyvitamin $D_3$ [M+H]+ precursor ion produced using method 300 is about 401.2. Although numerous product ions are produced, the Da/e of several of the most prevalent product ions produced using the system and methods described herein is about 159.1, 131.1, 105.1, or 91.1. The mass/charge ratio (Da/e) for the 25-hydroxyvitamin $D_2$ [M+H]+ precursor ion produced using method 300 is about 413.2 and the Da/e of the most prevalent product ions produced using the system and methods described herein is about 131.1, 107.1, 105.1, or 91.1.

In one embodiment, the method 300 further includes purifying, ionizing, fragmenting, and detecting one or more vitamin D metabolites selected from the group consisting of 1,25-dihydroxyvitamin $D_3$, 24,25-dihydroxyvitamin $D_3$, 1,25-dihydroxyvitamin $D_2$, and 24,25-dihydroxyvitamin $D_2$.

According to the present method 300, the mobile phase buffer contains a volatile additive capable of stabilizing and/or promoting formation of protonated ions specific to each of 25-hydroxyvitamin $D_3$ and 25-hydroxyvitamin $D_2$. In one embodiment, the volatile additive includes ammonium ions or forms ammonium ions in the mobile phase buffer. In one embodiment, the additive is ammonium formate or ammonium acetate. In one embodiment, the additive is included in the mobile phase buffer in an amount ranging from about 2 mM to about 10 mM, or about 4 mM to about 8 mM, or about 10 mM.

Without being tied to one theory, it is believed that ammonium ions may participate in the formation of the protonated ion form of the analyte of interest (i.e., 25-hydroxyvitamin $D_3$, 25-hydroxyvitamin $D_2$, or another vitamin D metabolite) by donating a proton to the analyte as the ammonium and the analyte exit the ESI and are desolvated into the gas phase. Neutral analytes can be ionized by accepting a proton from the ammonium ions in the gas phase due to the fact that the analyte has a higher proton affinity then the ammonia. This type of reaction is well documented by the use of traditional chemical ionization (CI) techniques.

EXAMPLES 25-hydroxyvitamin $D_3$ and 25-hydroxyvitamin $D_2$ were purchased from Sigma (St. Louis, Mo.). A 2 mg/mL stock solution was made by dissolving 25-hydroxyvitamin $D_3$ and 25-hydroxyvitamin $D_2$ in methanol. All other concentrations were made by serial dilutions into methanol (neat) or stripped serum (matrix). Suitable stripped sera include Fetal Bovine Serum Charcoal Stripped serum (Sigma Aldrich, Cat. No. F6765) and human serum, antibody stripped. Standards and QCs were made in stripped serum. Standards were made with a range of 1-300 ng/mL and QCs were made 2, 120 and 240 ng/mL. Hexadeuterated 25-hydroxyvitamin $D_3$ ($d_6$-25-OH $D_3$) was purchased from Medical Isotopes (Cat. No. D2831) and used as an internal standard (IS). A 1 mg/mL IS stock solution was made in methanol and diluted to 140 ng/mL with methanol for the working IS stock solution. All stock and working solutions were stored at −80° C.

Samples were prepared by adding 200 µL of working internal standard to 100 µL of sample followed by vortex mixing for 15 sec at max speed and centrifugation at 4000 rcf for 2 min. 150 µL of supernatant was then transferred into autosampler vials for analysis.

HPLC was performed with Thermo Scientific Transend TX system (Thermo Fisher Scientific) using a 0.5×50 mm Cyclone P column (Thermo Fisher Scientific) for on-line sample clean-up and a 2.1×50 mm, 1.9 µm Hypersil Gold PFP™ or a 2.1×50 mm, 2.6 µm Accucore PFP™ analytical column (Thermo Fisher Scientific). This system is a dual column system that can perform HPLC or Ultra High Pressure Liquid Chromatography (UHPLC) and utilizes TurboFlow technology to perform on-line clean-up. Other systems are suitable including those wherein sample clean-up is performed off-line. The mass spectra were acquired on a Thermo Scientific Vantage triple quadrupole mass spectrometer (Thermo Fisher Scientific). Mobile phase A was 10 mM ammonium formate with 0.01% formic acid in water. Mobile phase B was 10 mM ammonium formate with 0.01% formic acid in methanol. Mobile phase C was 45:45:10 isopropanol: acetonitrile:acetone that is used to wash the columns.

10 μL-100 μl of sample was injected onto the turbulent flow chromatography ("TFC") column with 80% mobile phase A at 1.5 mL/min. Large molecules, such as proteins, are washed to waste while small molecules (>1000 Da) are retained on the column. Once the sample has been separated from most of the biological matrix, the valves switch and the sample is eluted from the TFC column with 100% mobile phase B at 0.2 mL/min. The flow from the TFC column is teed to a second UHPLC pump flowing 80% mobile A at 0.5 mL/min. The mixed flow from both pumps reduces the amount of organic seen by the analytical column such that the analyte of interest is focused at the head of the analytical column. Once the analyte of interest is transferred to the analytical column, the valves are switched again, isolating the two columns from each other. The TFC column is washed and equilibrated for the next sample and a 20-100% mobile phase B gradient is run on the analytical column to elute the analyte of interest into the mass spectrometer for analysis.

The mass spectrometer parameters are as follows. Spray voltage 5000, Vaporizer temperature 400, sheath gas pressure 60, aux gas pressure 35, capillary temperature 199, S-lens amplitude 55. Full scan Q1 data was acquired to look at the relative ion abundances of the methods tested and Selective Reaction Monitoring (SRM) was used for quantitative comparison.

The SRM transitions used were as follows; 25-hydroxyvitamin $D_3$: 401.352 parent, 91.122, 105.133, 159.139, 365.425 product ions. 25-hydroxyvitamin $D_2$: 91.089, 95.158, 105.104, 159.149 product ions. $d_6$-25-OH $D_3$: 407.380 parent, 107.115, 133.105, 147.199, 159.190 product ions. Quadrupole 1 (Q1) (full width at half maximum, FWHM) was set at 0.7 and quadrupole 3 (Q3) (FWHM) was set at 0.7. Scan width (Da/e) 0.01, scan time (s) 0.05. Collision gas pressure was set at 1.5 mTorr.

Referring now to FIG. 4, a full MS/MS product ion spectrum for 25-hydroxy Vitamin $D_2$ is illustrated showing product ions that can be detected for 25-hydroxy Vitamin $D_2$. The illustrated product ions, which include the ions discussed above, can be used to detect and/or quantify the presence of 25-hydroxy Vitamin $D_2$ in a sample. The full MS/MS product ion spectrum for 25-hydroxy Vitamin $D_2$ depicts the [M+H]+ parent ion of 25-hydroxy Vitamin $D_2$ at a Da/e of approximately 413 and major and minor product ions at Da/e of approximately 395, 377, 355, 337, 271, 255, 199, 175, 159, 147, 145, 133, 131, 121, 119, 117, 107, 105, 95, 93, 91, 81, 79, 67, 59, and 55.

Figure 5:
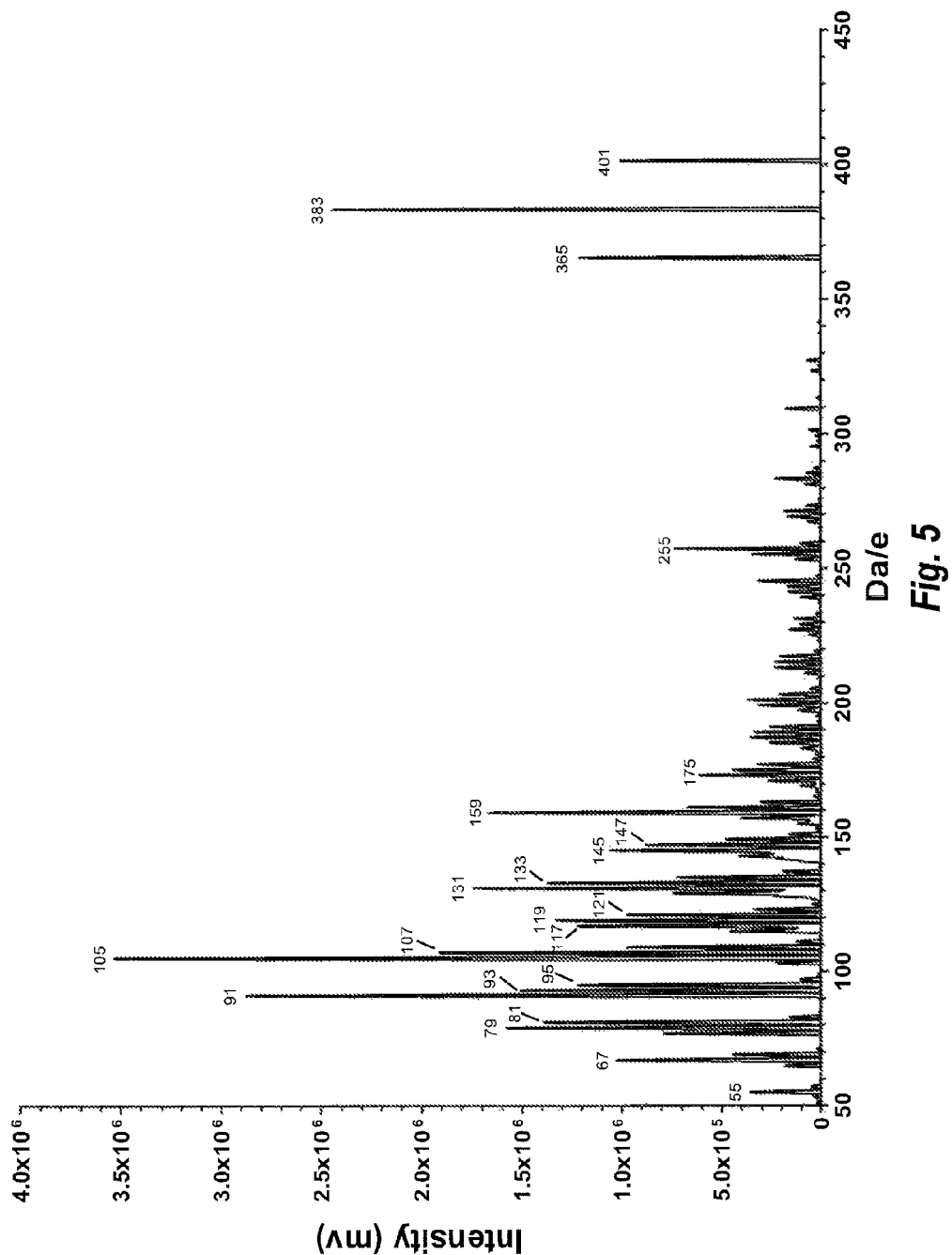
FIG. 5 depicts an MS/MS product ion spectrum of Da/e 401 for 25-hydroxy Vitamin $D_3$.
Figures 7A, 7B:
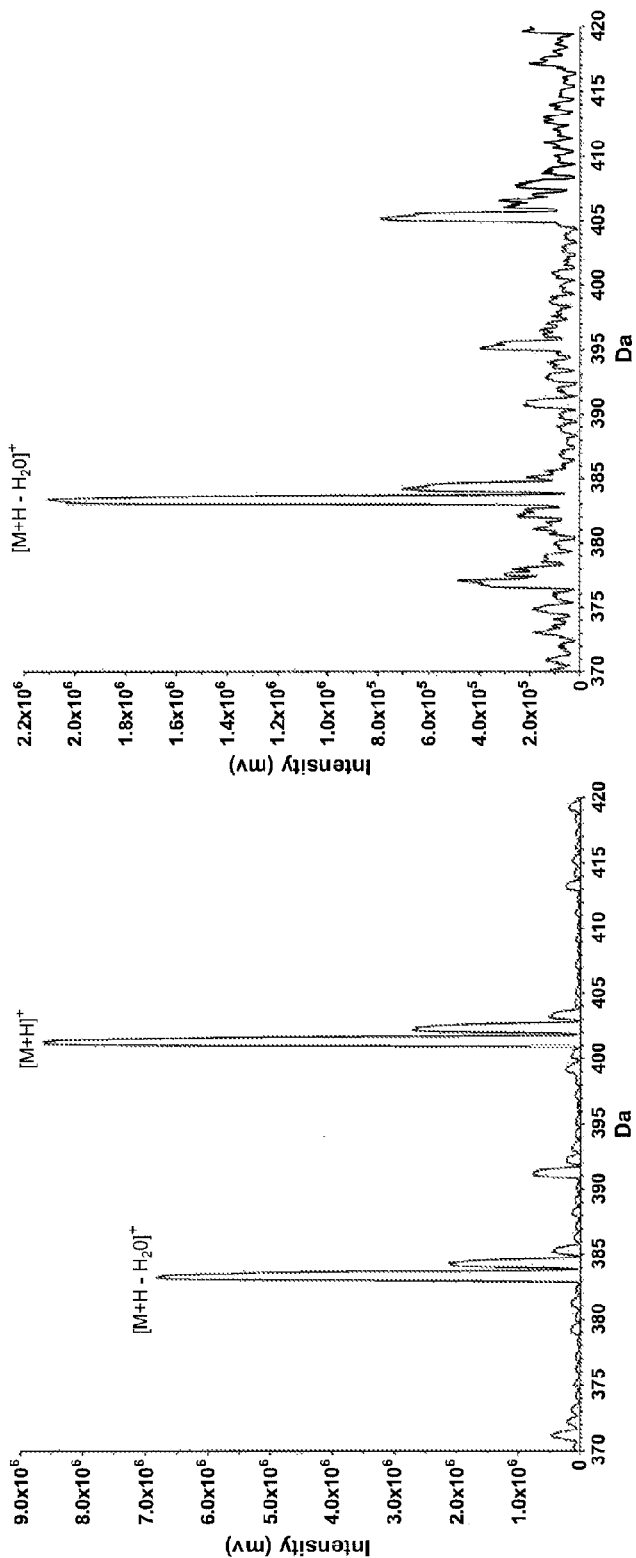
FIG. 7A depicts an ESI full scan spectrum of the molecular ion region for 25-OH $D_3$ using ammonium formate.
FIG. 7B depicts an ESI full scan spectrum of the molecular ion region for 25-OH $D_3$ using formic acid.
Figures 8A, 8B:
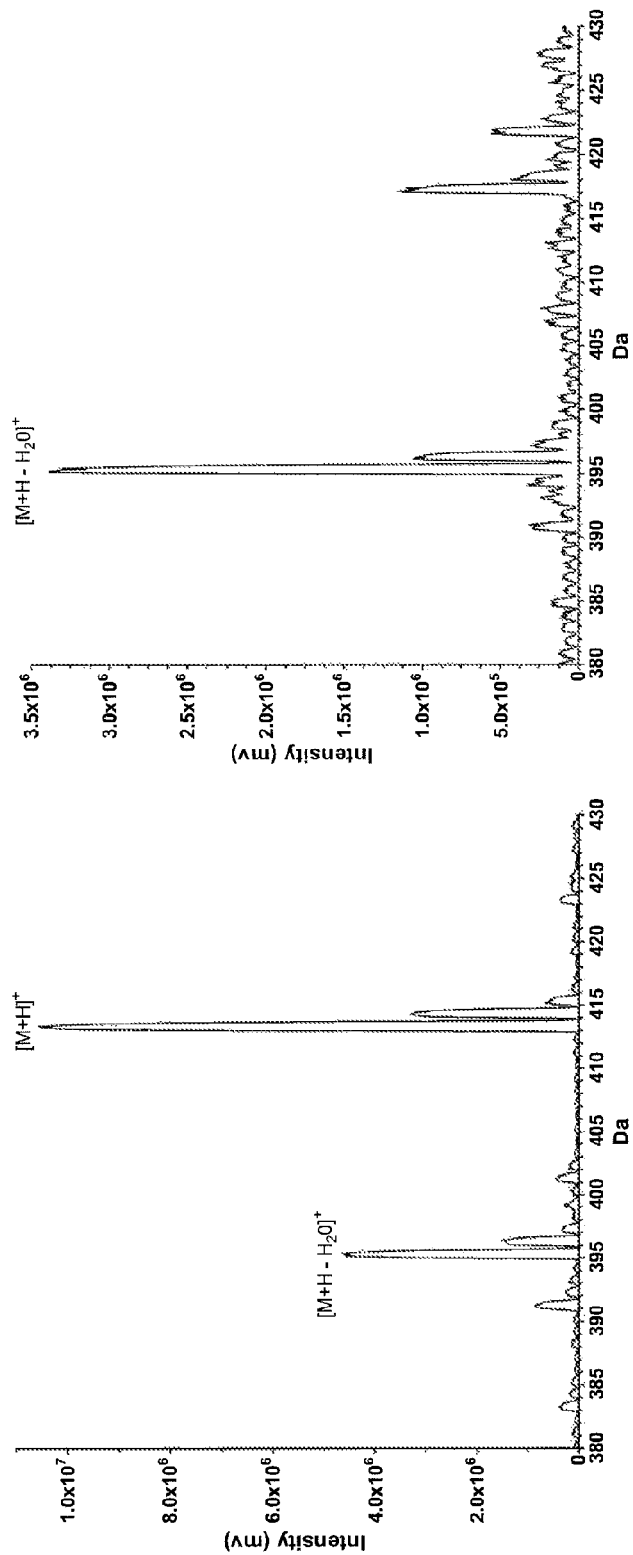
FIG. 8A depicts an ESI full scan spectrum of the molecular ion region for 25-OH $D_2$ using ammonium formate.
FIG. 8B depicts an ESI full scan spectrum of the molecular ion region for 25-OH $D_2$ using formic acid.
Figures 10A, 10B:
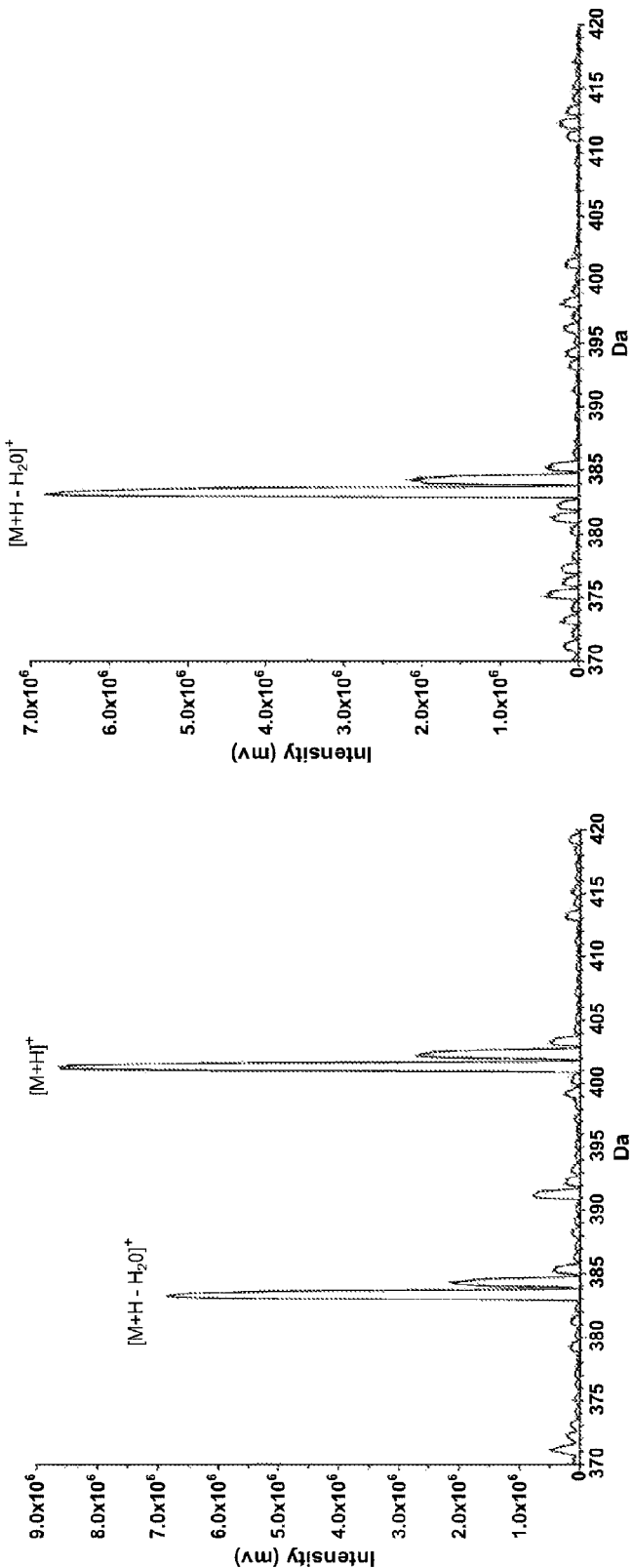
FIG. 10A depicts an ESI full scan spectrum of the molecular ion region for 25-OH $D_3$ using ammonium formate.
FIG. 10B depicts an APCI full scan spectrum of the molecular ion region for 25-OH $D_3$ using ammonium formate.

Referring now to FIG. 5, a full MS/MS product ion spectrum for 25-hydroxy Vitamin $D_3$ is illustrated is illustrated showing product ions that can be detected for 25-hydroxy Vitamin $D_3$. The illustrated product ions, which include the ions discussed above, can be used to detect and/or quantify the presence of 25-hydroxy Vitamin $D_3$ in a sample. The full MS/MS product ion spectrum for 25-hydroxy Vitamin $D_3$ depicts the [M+H]+ parent ion of 25-hydroxy Vitamin $D_3$ at a Da/e of approximately 401 and major and minor product ions at Da/e of approximately 383, 365, 255, 175, 159, 147, 145, 133, 131, 121, 119, 117, 107, 105, 95, 93, 91, 81, 79, 67, and 55.

Referring now to FIG. 6, a full MS/MS product ion spectrum for hexadeuterated 25-hydroxyVitamin $D_3$ is illustrated. Hexadeuterated 25-hydroxy Vitamin $D_3$ can be used as an internal standard for detection and quantitation of 25-hydroxy Vitamin $D_2$ and 25-hydroxy Vitamin $D_3$ and other vitamin D metabolites. The full MS/MS product ion spectrum for hexadeuterated 25-hydroxy Vitamin $D_3$ depicts the [M+H]+ parent ion of hexadeuterated 25-hydroxyVitamin $D_3$ at a Da/e of approximately 407 (i.e., 6 mass units greater than the parent ion of 25-hydroxy Vitamin $D_3$) and major and minor product ions at Da/e of approximately 389, 371, 213, 185, 173, 161, 159, 147, 145, 135, 133, 131, 119, 117, 109, 107, 105, 95, 93, 91, 81, 79, and 67.

Comparison of full scan data for the [M+H]+ ion using ammonium formate in the mobile phase verses the [M+H-$H_2O$]+ for Vitamin $D_2$ and $D_3$ using formic acid in the mobile phase are shown in the FIGS. 7A-8B. Note that the addition of an ammonium source significantly increases the sensitivity of detection and significantly improves the signal-to-noise ratio. Note also that the [M+H]+ ion is not detected without ammonium ions.

Comparison of full scan data for the [M+H]+ ion and the [M+H-$H_2O$]+ ion using ammonium formate in the mobile phase with ESI verses APCI are shown in the FIGS. 9A-10B. Note that even in the presence of ammonium ions, the [M+H]+ ion is not detected without ESI.

Figures 11A, 11B:
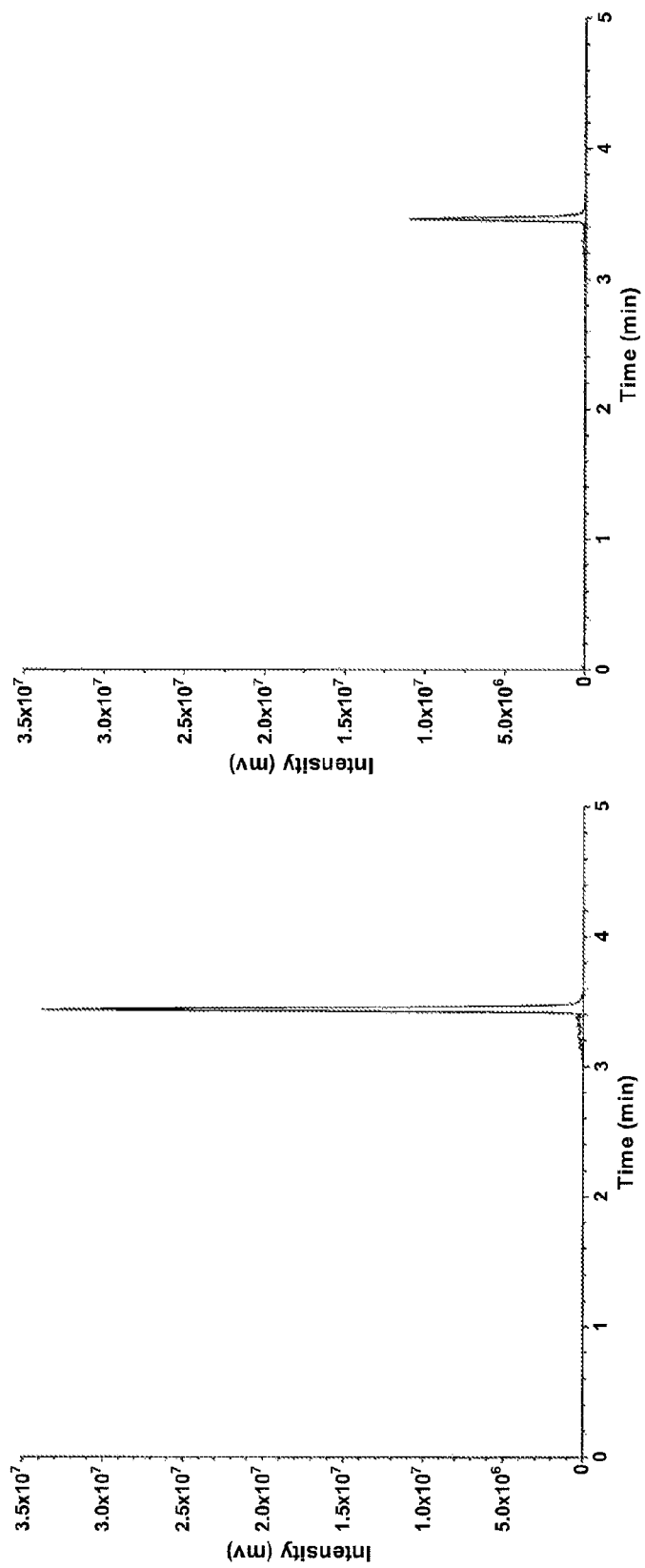
FIG. 11A depicts the selected reaction monitoring ("SRM") signal from 25-OH $D_2$ using ESI to produce the [M+H]+ molecular ion.
FIG. 11B depicts the SRM signal from 25-OH $D_2$ using APCI to produce the [M+H–$H_2O$]+ water loss ion.

More important to the quantitation using MS/MS is the comparison of the SRM data from using the [M+H]+ and [M+H-$H_2O$]+ as the precursor ions. Those comparisons are shown in FIGS. 11A-12B. It is clear that the use of the [M+H]+ ion formed by the presence of ammonium ions in the mobile by electrospray has higher sensitivity then using the [M+H-$H_2O$]+ ion by APCI. The data in FIGS. 11A and 11B illustrate that detection and quantitation of 25-hydroxyvitamin $D_2$ with the [M+H]+ ion from ESI is about 3.5 times more sensitive than detection with the [M+H-$H_2O$]+ from APCI. The data in FIGS. 12A and 12B illustrate that detection and quantitation of 25-hydroxyvitamin $D_3$ with the [M+H]+ ion from ESI is about 8 times more sensitive than detection with the [M+H-$H_2O$]+ from APCI.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method for detecting and/or quantifying at least one vitamin D metabolite including 25-hydroxyvitamin $D_3$ and 25-hydroxyvitamin $D_2$ in a sample by liquid chromatography-mass spectrometry, the method comprising:
   purifying 25-hydroxyvitamin $D_3$ and 25-hydroxyvitamin $D_2$, if present in the sample, by liquid chromatography using a mobile phase buffer containing a source of ammonium ions to stabilize and/or promote formation of a protonated molecular ion specific to each of 25-hydroxyvitamin $D_3$ and 25-hydroxyvitamin $D_2$;
   ionizing the 25-hydroxyvitamin $D_3$ and 25-hydroxyvitamin $D_2$ in a mass spectrometer by electrospray ionization to produce the protonated molecular ion specific to each of 25-hydroxyvitamin $D_3$ and 25-hydroxyvitamin $D_2$, wherein the protonated molecular ion of 25-hydroxyvitamin $D_3$ has a mass/charge ratio (Da/e) of about 401.2 and the protonated molecular ion of 25-hydroxyvitamin $D_2$ precursor ion has a Da/e of about 413.2;

fragmenting the protonated molecular ions to produce prevalent product ions specific to each of 25-hydroxyvitamin $D_3$ and 25-hydroxyvitamin $D_2$, wherein the prevalent product ions specific to 25-hydroxyvitamin $D_3$ have a Da/e of about 159.1, 131.1, 105.1, and 91.1 and the prevalent product ions specific to 25 hydroxyvitamin $D_2$ have a Da/e of about 131.1, 107.1, 105.1, and 91.1, wherein the product ions specific to each of 25-hydroxyvitamin $D_3$ and 25-hydroxyvitamin $D_2$ are formed by fragmentation of the protonated molecular ion without water loss; and detecting and/or quantifying a presence or an amount of at least one protonated molecular ion or product ion specific to each of 25-hydroxyvitamin $D_3$ and 25-hydroxyvitamin $D_2$, wherein the presence or quantity of the detected ions is related to the presence or quantity of 25-hydroxyvitamin $D_3$ and 25-hydroxyvitamin $D_2$ in the sample.

2. The method of claim 1, further comprising purifying, ionizing, fragmenting, and detecting one or more vitamin D metabolites in the sample selected from the group consisting of 1,25-dihydroxyvitamin $D_3$, 24,25-dihydroxyvitamin $D_3$, 1,25-dihydroxyvitamin $D_2$, and 24,25-dihydroxyvitamin $D_2$.

3. The method of claim 1, wherein the source of ammonium ions includes ammonium ions or forms ammonium ions in the mobile phase buffer.

4. The method of claim 3, wherein the source of ammonium ions comprises ammonium formate or ammonium acetate.

5. The method of claim 4, wherein the source of ammonium ions is included in the mobile phase buffer in an amount ranging from about 2 mM to about 10 mM.

* * * * *